US009936697B2

(12) United States Patent
Hopkins et al.

(10) Patent No.: US 9,936,697 B2
(45) Date of Patent: Apr. 10, 2018

(54) FUNGICIDAL COMPOSITIONS

(71) Applicant: Dow AgroSciences LLC, Indianapolis, IN (US)

(72) Inventors: Derek J. Hopkins, New Plymouth (NZ); Cheryl Ann Cathie, New Plymouth (NZ); Todd Mathieson, Indianapolis (IN); Neil Foster, Drusenheim (FR)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/984,207

(22) Filed: Dec. 30, 2015

(65) Prior Publication Data
US 2016/0183528 A1 Jun. 30, 2016

Related U.S. Application Data

(60) Provisional application No. 62/098,202, filed on Dec. 30, 2014, provisional application No. 62/098,199, filed on Dec. 30, 2014, provisional application No. 62/098,224, filed on Dec. 30, 2014.

(51) Int. Cl.
*A01N 43/40* (2006.01)
*A01N 43/653* (2006.01)

(52) U.S. Cl.
CPC ............ *A01N 43/40* (2013.01); *A01N 43/653* (2013.01)

(58) Field of Classification Search
CPC ...................................................... A01N 43/56
See application file for complete search history.

(56) References Cited

U.S. PATENT DOCUMENTS

| | | | |
|---|---|---|---|
| 4,213,776 A | 7/1980 | Giilck et al. | |
| 5,401,871 A * | 3/1995 | Feldmann-Krane | .. C07F 7/0847 504/362 |
| 6,355,660 B1 | 3/2002 | Ricks et al. | |
| 6,436,421 B1 * | 8/2002 | Schindler | ............... A01N 25/24 424/405 |
| 6,521,622 B1 | 2/2003 | Ricks et al. | |
| 6,706,740 B2 | 3/2004 | Ricks et al. | |
| 6,861,390 B2 | 3/2005 | Meyer et al. | |
| 6,916,932 B2 | 7/2005 | Meyer et al. | |
| 6,927,225 B2 | 8/2005 | Ricks et al. | |
| 7,034,035 B2 | 4/2006 | Ricks et al. | |
| 7,183,278 B1 | 2/2007 | Imamura et al. | |
| 7,250,389 B1 | 7/2007 | Sakanaka et al. | |
| 8,785,479 B2 | 7/2014 | Meyer et al. | |
| 8,835,462 B2 | 9/2014 | Meyer et al. | |
| 8,883,811 B2 | 11/2014 | Owen et al. | |
| 9,265,253 B2 | 2/2016 | Li et al. | |
| 2002/0177578 A1 | 11/2002 | Ricks et al. | |
| 2003/0018012 A1 | 1/2003 | Ricks et al. | |
| 2003/0018052 A1 | 1/2003 | Ricks et al. | |
| 2003/0022902 A1 | 1/2003 | Ricks et al. | |
| 2003/0022903 A1 | 1/2003 | Ricks et al. | |
| 2004/0034025 A1 | 2/2004 | Ricks et al. | |
| 2004/0048864 A1 | 3/2004 | Ricks et al. | |
| 2004/0171838 A1 | 9/2004 | Meyer et al. | |
| 2004/0186296 A1 | 9/2004 | Niyaz et al. | |
| 2004/0192924 A1 | 9/2004 | Meyer et al. | |
| 2005/0239873 A1 | 10/2005 | Hockenbery et al. | |
| 2006/0040995 A1 | 2/2006 | Bacque et al. | |
| 2007/0060579 A1 | 3/2007 | Wachendorff-Neumann et al. | |
| 2007/0066629 A1 | 3/2007 | Tormo i Blasco et al. | |
| 2007/0087937 A1 * | 4/2007 | Leatherman | ........... A01N 25/30 504/101 |
| 2008/0070985 A1 | 3/2008 | Derrer et al. | |
| 2008/0293798 A1 | 11/2008 | Dietz et al. | |
| 2008/0318785 A1 | 12/2008 | Koltzenburg | |
| 2009/0203770 A1 | 8/2009 | Hockenberry et al. | |
| 2009/0306142 A1 | 12/2009 | Carson et al. | |
| 2010/0016163 A1 * | 1/2010 | Keiper | ................... A01N 25/30 504/206 |
| 2011/0034493 A1 | 2/2011 | Boebel et al. | |
| 2011/0053891 A1 | 3/2011 | Boebel et al. | |
| 2011/0053966 A1 | 3/2011 | Klittich et al. | |
| 2011/0070278 A1 | 3/2011 | Lopez | |

(Continued)

FOREIGN PATENT DOCUMENTS

| | | |
|---|---|---|
| CN | 102638989 | 8/2012 |
| EP | 1054011 | 11/2000 |

(Continued)

OTHER PUBLICATIONS

Pubchem, Substance Record for SID 74383515. Deposit Date Jun. 11, 2009 [retrieved on May 25, 2016] Retrieved from internet. <URL:https://pubchem.ncbi.nlm.nih.gov/substance/74383515#section=Top>.
Gisi, U., The American Phytopathological Society, vol. 86, No. 11, 1996, p. 1273.
Huang, et al., Synergistic Interactions between Chitinase ChiCW and Fungicides Against Plant Fungal Pathogens, J. Microbiol. Biotechnol., 2008, 18(4) 784-787.
Backman, P., Fungicide Formulation: Relationship to Biological Activity, 1978, 16, 211-237.
Latin, et al, Re-Examining Fungicide Synergism for Dollar Spot Control, GCM, 2008, 84-87.

(Continued)

*Primary Examiner* — San Ming R Hui
(74) *Attorney, Agent, or Firm* — Charles W. Arnett; Faegre Baker Daniels LLP

(57) ABSTRACT

Described herein are fungicidal compositions in the form of an emulsifiable concentrates that include a first fungicidal compound, optionally, at least one additional fungicidal compound, two or more surfactants and a water immiscible organic solvent comprised of a mixture of organic compounds including at least one acetate ester and at least one N,N-dialkylcarboxamide. The compositions are homogeneous, stable upon storage, and upon dilution in water form stable emulsions that can be sprayed onto plants to control important fungal diseases.

21 Claims, No Drawings

(56) References Cited

U.S. PATENT DOCUMENTS

| | | |
|---|---|---|
| 2011/0082039 A1 | 4/2011 | Keeney et al. |
| 2011/0082160 A1 | 4/2011 | Owen |
| 2011/0082162 A1 | 4/2011 | Lorsbach et al. |
| 2011/0306644 A1 | 12/2011 | Hoekstra et al. |
| 2012/0035054 A1 | 2/2012 | Ehr et al. |
| 2012/0245031 A1 | 9/2012 | Gewehr et al. |
| 2013/0090298 A1 | 4/2013 | Lee et al. |
| 2013/0296371 A1 | 11/2013 | Meyer et al. |
| 2013/0296372 A1 | 11/2013 | Owen et al. |
| 2013/0296373 A1 | 11/2013 | Meyer |
| 2013/0296374 A1 | 11/2013 | Owen et al. |
| 2013/0296375 A1 | 11/2013 | Meyer et al. |
| 2014/0128411 A1 | 5/2014 | Ogawa et al. |
| 2014/0187587 A1 | 7/2014 | Ouimette et al. |
| 2014/0187588 A1 | 7/2014 | Lalonde et al. |
| 2014/0187590 A1 | 7/2014 | Ouimette et al. |
| 2014/0275171 A1 | 9/2014 | Meyer, Jr. et al. |
| 2015/0065529 A1 | 3/2015 | Owen, Jr. et al. |
| 2015/0094341 A1 | 4/2015 | Li et al. |
| 2015/0183759 A1 | 7/2015 | DeLorbe et al. |

FOREIGN PATENT DOCUMENTS

| | | |
|---|---|---|
| EP | 1516874 | 3/2005 |
| WO | WO 2001/014365 | 3/2001 |
| WO | WO 200114339 | 3/2001 |
| WO | WO 03/011857 | 2/2003 |
| WO | WO 2007017416 | 2/2007 |
| WO | WO 2009040397 | 9/2008 |
| WO | WO 2011028657 | 3/2011 |
| WO | WO 2011044213 | 4/2011 |
| WO | WO 2011069893 | 6/2011 |
| WO | WO 2012/016972 | 2/2012 |
| WO | WO 2012016989 | 2/2012 |
| WO | WO 2012070015 | 5/2012 |
| WO | WO 2013/110002 | 7/2013 |
| WO | WO 2013/116251 | 8/2013 |
| WO | WO2013126948 A1 | 9/2013 |
| WO | WO 2015/103161 | 7/2015 |

OTHER PUBLICATIONS

O'Sullivan, et al., Fungicide Resistance—an Increasing Problem, Proceedings of National Tillage Conference 2007, Published by Crop Research Centre Oak Park Carlow, date Jan. 31, 2007, 14 pages.

Wilson, C.L. et al. "Fruit Volatiles Inhibitory to Monilinia fructicola and Botrytis cinerea" 1987, Plant Disease 71:316-319.

"Sulfonate" (http://www.hichem.com/product/showproduct.php?id=334639) Mar. 28, 2013, p. 1-4.

Koyanagi et al., "Bioisoterism, etc.," Synthesis and Chemistry of Agrochemicals IV; Baker, D. et al., 1995, 15-24.

Masashi Ueki et al., "UK-2A, B, C, and D, Novel Antifungal Antibiotics from *Streptomyces* sp. 517-02 I. Fermentation, Isolation, and Biological Properties," The Journal of Antibiotics, vol. 49, No. 7, Jul. 1996, pp. 639-634.

K. Tani et al., Journal of Antibiotics, vol. 55, No. 3, Mar. 2002, pp. 315-321.

Y. Usuki et al., Journal of Antibiotics, vol. 55, No. 6, Jun. 2002, pp. 607-610.

Anonymous, Synergistic Fungicidal Composition of Heterocyclic Aromatic Amides and Triazoles, ip.com, Electronic Publication, 2004, 11 pages.

Anonymous, Synergistic Fungicidal Composition of Heterocyclic Aromatic Amides and Triazoles, ip.com Journal, ip.com, Inc., West Henrietta, NY, US, Jul. 2004, 10 pages.

Z. Hu et al., Synthesis of Novel Analogues of Antimycin A3, Tetrahedron Letters 49 (2008), pp. 5192-5195.

Usuki, et al., "Semi-synthesis and biological evaluation of analogues of UK-2A, a novel antifungal antibiotic from *Steptomyces* sp. 517-02," Bioorganic & Medicinal Chemistry Letters, Pergamon, Amsterdam, KL, vol. 15, No. 8, Apr. 15, 2005, pp. 2011-2014, XP027801790.

Copenheaver, B.R., International Search Report and Written Opinion for PCT/US2015/068011, dated Mar. 7, 2016, 11 pages.

Copenheaver, B.R., International Search Report and Written Opinion for PCT/US2015/068018, dated Mar. 4, 2016, 11 pages.

Copenheaver, B.R., International Search Report and Written Opinion for PCT/US2015/068019, dated Mar. 7, 2016, 9 pages.

\* cited by examiner

FUNGICIDAL COMPOSITIONS

PRIORITY CLAIM

This application claims the benefit of U.S. Provisional Application No. 62/098,199, filed Dec. 30, 2014, U.S. Provisional Application No. 62/098,202, filed Dec. 30, 2014, and U.S. Provisional Application No. 62/098,224, filed Dec. 30, 2014, the complete disclosures of all of which are hereby expressly incorporated by reference.

FIELD OF THE INVENTION

Some aspects of the invention relate to emulsions which include fungicides and are suitable for use in agriculture.

BACKGROUND AND SUMMARY

Liquid pre-mix concentrates comprising two or more active ingredients are useful in a wide variety of agricultural applications. For example, two or more pesticidal active ingredients may be combined in order to control a wider spectrum of pests, or to utilize multiple modes of action, compared to the individual active ingredients alone.

Water insoluble pesticide active ingredients may be formulated in water as aqueous suspension concentrates (SC) or by dissolving the water insoluble pesticide in an organic solvent and forming an emulsifiable concentrate (EC). The preparation of these liquid, pre-mix concentrates can be challenging owing to chemical and/or physical instability issues.

Emulsifiable concentrate formulations, also known as emulsion concentrates or ECs, are widely used in crop protection. The disadvantages of some emulsifiable concentrates include their poor cold temperature stability and the pronounced tendency of the active ingredient to crystallize, owing to the low solubility of some active ingredients in the concentrate. It was an object of the present disclosure to provide an emulsifiable concentrate which overcomes these disadvantages.

Some aspects of the invention provide fungicidal compositions comprising: a fungicidal compound of the Formula:

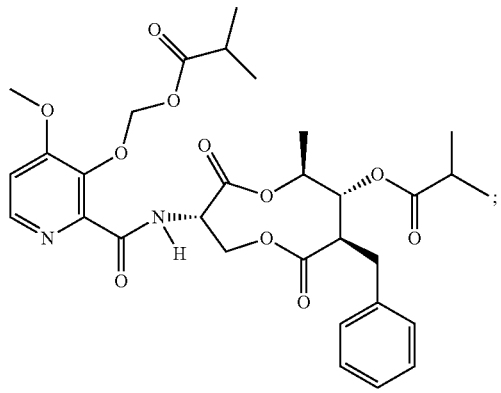 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

at least one ionic surfactant; at least one nonionic surfactant; an acetate ester; and an N,N-dialkylcarboxamide.

In certain embodiments, the described fungicidal composition may include at least one additional fungicidal compound.

In certain embodiments, the acetate ester and the N,N-dialkylcarboxamide together form a water immiscible organic solvent for the described fungicidal composition.

In certain embodiments, the described fungicidal composition forms a stable, homogenous emulsifiable concentrate that readily emulsifies and forms a stable emulsion without crystallization of the fungicidal compound when added to water.

In certain embodiments, the described composition may include an adjuvant that improves the fungicidal performance of the composition.

In certain embodiments, the described composition may include additional active ingredients and/or inert formulation ingredients.

Also provided herein is a method of controlling plant derived fungal pathogens or diseases comprising contacting the vegetation or an area adjacent thereto to prevent the growth of the fungal pathogens or diseases with a fungicidally effective amount of a fungicidal composition comprising: a fungicidal compound of the Formula:

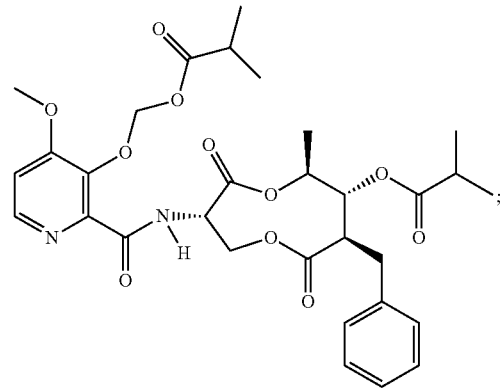 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

at least one ionic surfactant; at least one nonionic surfactant; an acetate ester; and an N,N-dialkylcarboxamide.

A first set of embodiments of the present disclosure includes fungicidal compositions comprising:
a) a fungicidal compound of the Formula

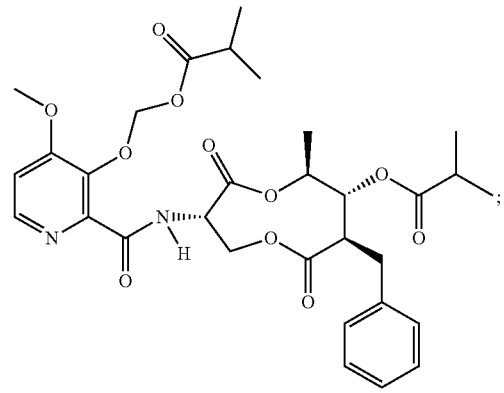 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

b) at least one ionic surfactant;
c) at least one nonionic surfactant;
d) at least one acetate ester; and
e) at least one N,N-dialkylcarboxamide.

A second set of embodiments includes the fungicidal compositions of the first set of embodiments, wherein the composition includes:

a) from about 1 gram per liter (g/L) to about 200 g/L of the fungicidal compound of the Formula

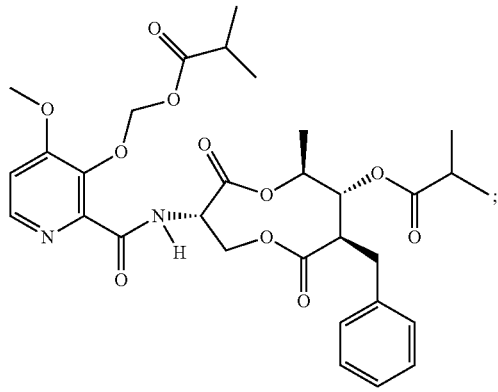 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

b) from about 1 g/L to about 100 g/L of the at least one ionic surfactant, wherein the at least one ionic surfactant includes at least one anionic surfactant;
c) from about 1 g/L to about 200 g/L of the at least one nonionic surfactant;
d) from about 50 g/L to about 700 g/L of the at least one acetate ester; and
e) from about 25 g/L to about 300 g/L of the at least one N,N-dialkylcarboxamide, wherein the at least one N,N-dialkylcarboxamide includes an N,N-dimethyl fatty acid amide.

A third set of embodiments includes the fungicidal composition of any of the first and/or the second set of embodiments, wherein the composition includes from about 1 gram per liter (g/L) to about 200 g/L of the fungicidal compound of the Formula:

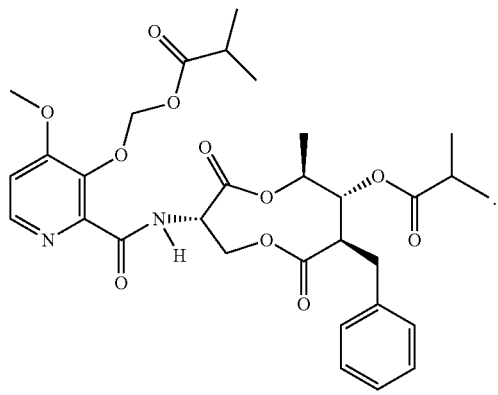 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

A fourth set of embodiments includes the fungicidal composition of any of the first through the third set of embodiments, wherein the composition includes from about 1 g/L to about 100 g/L of the at least one ionic surfactant, wherein the at least one ionic surfactant includes at least one anionic surfactant.

A fifth set of embodiments includes the fungicidal composition of any of the first through the fourth set of embodiments, wherein the composition includes from about 1 g/L to about 200 g/L of the at least one nonionic surfactant.

A sixth set of embodiments includes the fungicidal composition of any of the first through the fifth set of embodiments, wherein the composition includes from about 50 g/L to about 700 g/L of the at least one acetate ester.

A seventh set of embodiments includes the fungicidal composition of any of the first through the sixth set of embodiments, wherein the composition includes from about 25 g/L to about 300 g/L of the at least one N,N-dialkylcarboxamide, therein the at least one N,N-dialkylcarboxamide includes at least one of an N,N-dimethyl fatty acid amide.

An eighth set of embodiments includes the fungicidal composition of any of the first through the seventh set of embodiments, wherein the at least one acetate ester and the at least one N,N-dialkylcarboxamide together form a water immiscible organic solvent.

A ninth set of embodiments includes the fungicidal composition of any of the first through the eighth set of embodiments, wherein the weight ratio of the at least one acetate ester:the at least one N,N-dialkylcarboxamide ranges from about 1-10:1-10.

A tenth set of embodiments includes the fungicidal composition of any of the first through the ninth set of embodiments, wherein the weight ratio of the at least one acetate ester:the at least one N,N-dialkylcarboxamide ranges from about 1-5:1-2.

An eleventh set of embodiments includes the fungicidal composition of any of the first through the tenth set of embodiments, wherein the at least one acetate ester is selected from a group consisting of benzyl acetate, cyclohexylmethyl acetate and phenyl acetate.

A twelfth set of embodiments includes the fungicidal composition of any of the first through the eleventh set of embodiments, wherein the at least one N,N-dialkylcarboxamide is selected from a group consisting of N,N-dimethylhexanamide, N,N-dimethyloctanamide, N,N-dimethyldecanamide and N,N-dimethyldodecanamide.

A thirteenth set of embodiments includes the fungicidal composition of any of the first through the twelfth set of embodiments, further including at least one additional fungicidal compound.

A fourteenth set of embodiments includes the fungicidal composition of the thirteenth set of embodiments, wherein the at least one additional fungicidal compound is selected from a group consisting of azoxystrobin, bifujunzhi, coumethoxystrobin, coumoxystrobin, dimoxystrobin, enestroburin, enoxastrobin, fenaminstrobin, fenoxystrobin, flufenoxystrobin, fluoxastrobin, jiaxiangjunzhi, kresoximmethyl, mandestrobin, metominostrobin, orysastrobin, picoxystrobin, pyraclostrobin, pyrametostrobin, pyraoxystrobin, triclopyricarb, trifloxystrobin, methyl 2-[2-(2,5-dimethylphenyloxymethyl)phenyl]-3-methoxyacrylate, azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, imazalil, pefurazoate, prochloraz, triflumizole, pyrimidines, fenarimol, nuarimol, pyrifenox, and triforine.

A fifteenth set of embodiments includes the fungicidal composition of the thirteenth and/or the fourteenth embodiments, wherein the at least one additional fungicidal compound is selected from a group consisting of azoxystrobin, kresoxim-methyl, picoxystrobin, pyraclostrobin, trifloxystrobin, epoxiconazole, fenbuconazole, myclobutanil, propiconazole, prothioconazole, and tebuconazole.

A sixteenth set of embodiments includes the fungicidal composition of any one of thirteenth through the fifteenth set of embodiments, wherein the at least one additional fungicidal compound is selected from a group consisting of pyraclostrobin, prothioconazole and propiconazole.

A seventeenth set of embodiments includes the fungicidal composition of any of the first through the sixteenth set of embodiments, further including an adjuvant that improves the fungicidal performance of the composition selected from a group consisting of a non-ionic surfactant, a polyether modified organopolysiloxane and an alkyl phosphonate.

An eighteenth set of embodiments includes methods of controlling fungal plant pathogens or diseases comprising the steps of contacting the vegetation or an area adjacent thereto to prevent the growth of the fungal pathogens or diseases with a fungicidally effective amount of a fungicidal composition comprising:

a) a fungicidal compound of the Formula

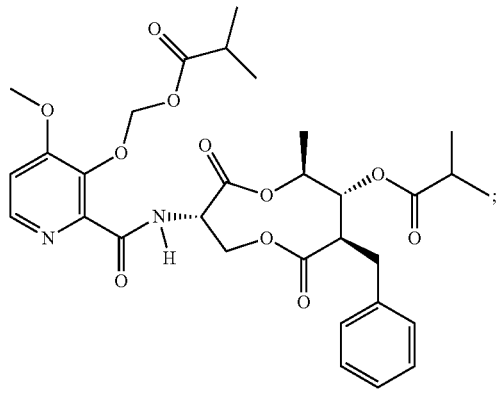 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

b) at least one ionic surfactant;
c) at least one nonionic surfactant;
d) at least one acetate ester; and
e) at least one N,N-dialkylcarboxamide.

A nineteenth set of embodiments includes the methods of the eighteenth set of embodiments, wherein the fungicidal composition includes from about 1 gram per liter (g/L) to about 200 g/L of the fungicidal compound of the Formula

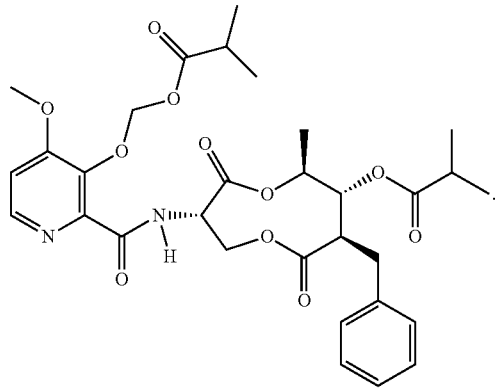 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

A twentieth set of embodiments includes the methods of the eighteenth and/or the nineteenth set of embodiments, wherein the fungicidal composition includes from about 1 g/L to about 100 g/L of an anionic surfactant of the at least one ionic surfactant, wherein the at least one ionic surfactant includes at least one anionic surfactant.

A twenty first set of embodiments includes the methods of any of the eighteenth through the twentieth set of embodiments, wherein the fungicidal composition includes from about 1 g/L to about 200 g/L of the at least one nonionic surfactant.

A twenty second set of embodiments includes the methods of any of the eighteenth through the twenty first set of embodiments, wherein the fungicidal composition includes from about 50 g/L to about 700 g/L of the acetate ester.

A twenty third set of embodiments includes the methods of any of the eighteenth through the twenty second set of embodiments, wherein the fungicidal composition includes from about 25 g/L to about 300 g/L of the at least one N,N-dialkylcarboxamide, wherein the at least one N,N-dialkylcarboxamide includes an N,N-dimethyl fatty acid amide.

A twenty fourth set of embodiments includes the method of any of the eighteenth through the twenty third set of embodiments, wherein the at least one acetate ester and the at least one N,N-dialkylcarboxamide together form a water immiscible organic solvent.

A twenty fifth set of embodiments includes the methods of any of the eighteenth through the twenty fourth set of embodiments, wherein the weight ratio of the at least one acetate ester:the at least one N,N-dialkylcarboxamide ranges from about 1-10:1-10.

A twenty sixth set of embodiments includes the methods of any of the eighteenth through the twenty fifth set of embodiments, wherein the weight ratio of the at least one acetate ester:the N,N-dialkylcarboxamide ranges from about 1-5:1-2.

A twenty seventh set of embodiments includes the methods of any of the eighteenth through the twenty sixth set of embodiments, wherein the at least one acetate ester is selected from a group consisting of benzyl acetate, cyclohexylmethyl acetate and phenyl acetate.

A twenty eighth set of embodiments includes the methods of any of the eighteenth through the twenty seventh set of embodiments, wherein the at least one N,N-dialkylcarboxamide is selected from a group consisting of N,N-dimethylhexanamide, N,N-dimethyloctanamide, N,N-dimethyldecanamide and N,N-dimethyldodecanamide.

A twenty ninth set of embodiments includes the methods of any of the eighteenth through the twenty eighth set of embodiments, wherein the water immiscible organic solvent includes benzyl acetate and one or more than one of a fatty acid N,N-dialkylcarboxamide.

A thirtieth set of embodiments includes the methods of any of the eighteenth through the twenty ninth set of embodiments, the fungicidal composition further comprising at least one additional fungicidal compound.

A thirty first set of embodiments includes the methods of any of the thirtieth set of embodiments, wherein the at least one additional fungicidal compound is selected from a group consisting of azoxystrobin, bifujunzhi, coumethoxystrobin, coumoxystrobin, dimoxystrobin, enestroburin, enoxastrobin, fenaminstrobin, fenoxystrobin, flufenoxystrobin, fluoxastrobin, jiaxiangjunzhi, kresoxim-methyl, mandestrobin, metominostrobin, orysastrobin, picoxystrobin, pyraclostrobin, pyrametostrobin, pyraoxystrobin, triclopyricarb, trifloxystrobin, methyl 2-[2-(2,5-dimethylphenvloxymethyl) phenyl]-3-methoxyacrylate, azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, imazalil, pefurazoate, prochloraz, triflumizole, pyrimidines, fenarimol, nuarimol, pyrifenox, and triforine.

A thirty second set of embodiments includes the methods of any of the thirtieth through the thirty first set of embodiments, wherein the at least one additional fungicidal compound is selected from a group consisting of azoxystrobin, kresoxim-methyl, picoxystrobin, pyraclostrobin, trifloxystrobin, epoxiconazole, fenbuconazole, myclobutanil, propiconazole, prothioconazole, and tebuconazole.

A thirty third set of embodiments includes the methods of any of the thirtieth through the thirty second set of embodiments, wherein the at least one additional fungicidal compound is selected from a group consisting of pyraclostrobin, prothioconazole and propiconazole.

A thirty fourth set of embodiments includes the methods of any of the eighteenth through the thirty third set of embodiments, the fungicidal composition further comprising an adjuvant that improves the fungicidal performance of the fungicidal composition selected from a group consisting of a non-ionic surfactant, a polyether modified organopolysiloxane and an alkyl phosphonate.

A thirty fifth set of embodiments includes the methods of any of the eighteenth through the thirty fourth set of embodiments, wherein the fungal plant pathogens include *Septoria tritici, Puccinia triticina, Mycosphaerella graminicola, Puccinia triticina, Puccinia striiformis, Venturia inaequalis, Ustilago maydis, Uncinula necator, Rhynchosporium secalis, Leptosphaeria nodorum, Magnaporthe grisea, Monilinia fructicola, Pseudoperonospora cubensis. Pseudocercosporella herpotrichoides. Phakopsora pachyrhizi, Phaeosphaeria nodorum, Blumeria graminis tritici, Blumeria graminis hordei, Erysiphe cichoracearum, Ezysiphe graaminis, Glomerella lagenarium, Cercospora beticola, Alternaria solani, Rhizoctonia solani, Plasmopara viticola, Phytophthora infestans, Pyricularia oryzae*, and *Pyrenophora teres.*

A thirty sixth set of embodiments includes the methods of any of the eighteenth through the thirty fifth set of embodiments, wherein the fungal plant diseases include anthracnose, blasts, *botrytis*, brown rust, blister smut, brown rot, downy mildew, *fusarium*, powdery mildew, rusts, glume blotch, leaf blotch, net blotch, sheath blight, stripe rust, scab, eye spot, leaf spot, early blight, and late blight.

A thirty seventh set of embodiments includes the compositions or methods of any of the eighteenth through the thirty sixth set of embodiments, wherein the at least one ionic surfactant is an anionic surfactant selected from a group consisting of an alkali, alkaline earth and ammonium salt of an alkylarylsulfonic acid.

A thirty eighth set of embodiments includes the compositions or methods of any of the eighteenth through the thirty seventh set of embodiments, wherein the at least one non-ionic surfactant is selected from a group consisting of an alcohol initiated EO/PO block copolymer and an alcohol ethoxylate.

A thirty ninth set of embodiments includes fungicidal compositions comprising:

a) a fungicidal compound of the Formula

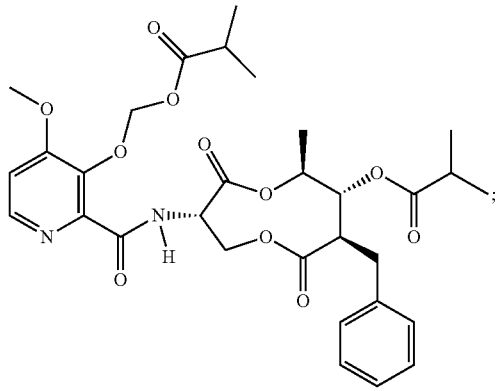 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

b) a calcium salt of an alkylaryl sulfonate;
c) an alcohol initiated EO/PO block copolymer;
d) a tridecyl alcohol ethoxylate;
e) a polyether modified organopolysiloxane;
f) benzyl acetate; and
g) an N,N-dimethyl fatty acid amide.

A fortieth set of embodiments includes fungicidal compositions comprising:

a) a fungicidal compound of the Formula

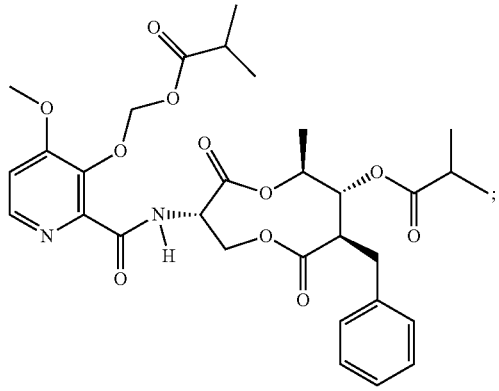 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

b) prothioconazole;
c) a calcium salt of an alkylaryl sulfonate;
d) an alcohol initiated EO/PO block copolymer;
e) a tridecyl alcohol ethoxylate;
f) a polyether modified organopolysiloxane;
g) benzyl acetate; and
h) an N,N-dimethyl fatty acid amide.

A forty first set of embodiments includes fungicidal compositions comprising:

a) a fungicidal compound of the Formula

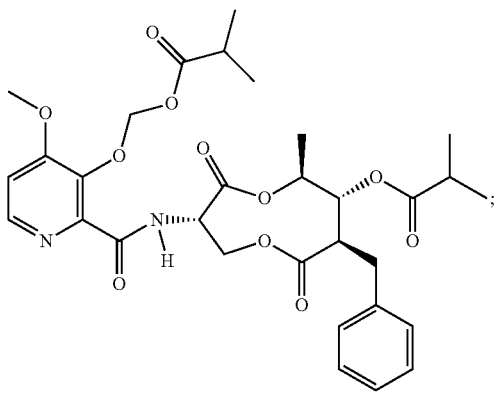 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

b) pyraclostrobin;
c) an calcium salt of an alkylaryl sulfonate;
d) an alcohol initiated EO/PO block copolymer;
e) a tridecyl alcohol ethoxylate;
f) a polyether modified organopolysiloxane;
g) benzyl acetate; and
h) an N,N-dimethyl fatty acid amide.

DETAILED DESCRIPTION

Some aspects of the invention described herein include fungicidal compositions in the form of an emulsifiable concentrate (i.e., an emulsion concentrate or EC) that includes at least one fungicidal compound, two or more surfactants and a water immiscible organic solvent comprised of a mixture of organic compounds including an acetate ester, an N,N-dialkylcarboxamide and optionally, at least one of a ketone and an alcohol. The described fungicidal composition exhibits good storage stability and readily forms a stable, homogenous emulsion upon dilution into a spray solution of water. The described fungicidal composition exhibits protectant and curative control of the important fungal diseases Septoria tritici (wheat leaf blotch) and Puccinia triticina (wheat brown rust) when utilized in spray applications.

Unless specifically or implicitly stated otherwise the term 'about' as used herein means plus or minus 10 percent. For example, 'about 1.0' encompasses the range of 0.9 to 1.1.

One exemplary embodiment provided herein is a fungicidal composition comprising:

a. a fungicidal compound of the Formula

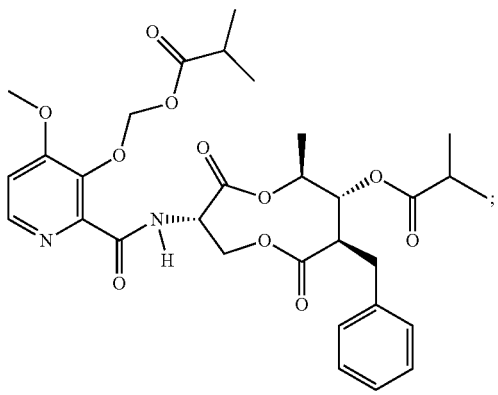 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

b. at least one ionic surfactant;
c. at least one nonionic surfactant;
d. an acetate ester; and
e. an N,N-dialkylcarboxamide.

A. FIRST FUNGICIDAL COMPOUND

One of the fungicidal compositions described herein is comprised of a first fungicidal compound of the Formula

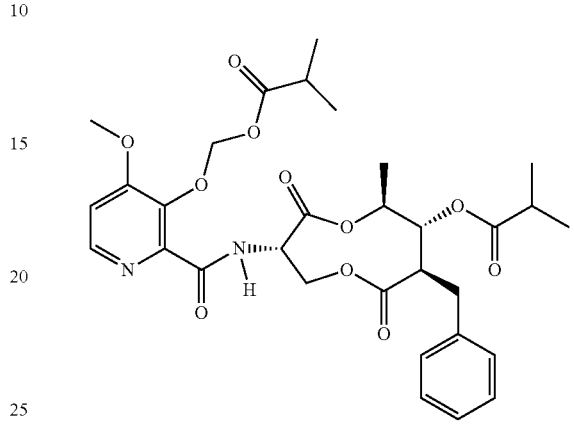

which is a chemical derivative of the natural product UK-2A as described in U.S. Pat. No. 6,861,390 (the disclosure of which is hereby incorporated by reference in its entirety), and has the Chemical Abstracts (CAS) Number 517875-34-2 and the CAS name: propanoic acid, 2-methyl-, [[4-methoxy-2-[[[(3S,7R,8R,9S)-9-methyl-8-(2-methyl-1-oxopropoxy)-2,6-dioxo-7-(phenylmethyl)-1,5-dioxonan-3-yl]amino]carbonyl]-3-pyridinyl]oxy]methyl ester. The first fungicidal compound exhibits biological control of certain fungal diseases such as, for example, Septoria tritici (SEPTTR; wheat leaf blotch) and Puccinia triticina (PUCCRT; wheat brown rust). The first fungicidal compound will be referred to herein as Compound A.

In some embodiments the fungicidal compositions described herein may comprise, with respect to the composition, from about 1 gram of active ingredient per liter (g ai/L) to about 200 g ai/L, from about 5 g ai/L to about 175 g ai/L, from about 10 g ai/L to about 150 g ai/L, from about 20 g ai/L to about 125 g ai/L, from about 20 g ai/L to about 100 g ai/L, from about 20 g ai/L to about 90 g ai/L, from about 30 g ai/L to about 90 g ai/L, from about 40 g ai/L to about 90 g ai/L, from about 40 g ai/L to about 80 g ai/L, from about 45 g ai/L to about 75 g ai/L, or from about 50 g ai/L to about 70 g ai/L of Compound A. The fungicidal compositions described herein may also comprise, with respect to the composition, from about 30 g ai/L to about 150 g ai/L, from about 40 g ai/L to about 150 g ai/L, from about 50 g ai/L to about 150 g ai/L, from about 60 g ai/L to about 150 g ai/L, from about 70 g ai/L to about 150 g ai/L, from about 80 g ai/L to about 150 g ai/L, from about 90 g ai/L to about 150 g ai/L, from about 100 g ai/L to about 150 g ai/L, from about 125 g ai/L to about 150 g ai/L, from about 50 g ai/L to about 140 g ai/L, from about 50 g ai/L to about 130 g ai/L, from about 50 g ai/L to about 120 g ai/L, from about 50 g ai/L to about 110 g ai/L, from about 50 g ai/L to about 100 g ai/L, from about 50 g ai/L to about 90 g ai/t, or from about 50 g ai/L to about 80 g ai/L of Compound A.

B. SURFACTANTS

The fungicidal composition described herein may include more than one surfactant which may include one or more than one each of an ionic and a non-ionic surfactant. Such surfactants may be used as an emulsifier, dispersant, solubilizer, wetter, penetrant, protective colloid, or for other purposes. Examples of surfactants are listed in McCutcheon's, Vol. 1: Emulsifiers & Detergents, McCutcheon's Directories, Glen Rock. USA, 2008 (International Ed. or North American Ed.). Since the described fungicidal composition is an emulsifiable concentrate (EC), surfactants are used to emulsify the EC when it is added to spray water so it forms a stable and homogeneous emulsion that can be readily applied by spray application to control target pests.

Suitable ionic surfactants for use with the fungicidal composition described herein may include anionic surfactants such as alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignin sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates. Preferred anionic surfactants are sulfates and sulfonates.

In some embodiments the ionic surfactant for use with the fungicidal composition described herein may include an anionic surfactant such as an alkali, alkaline earth or ammonium salt of an alkylarylsulfonic acid such as sulfonate salts of dodecyl- and/or tridecylbenzenes, sulfonate salts of naphthalenes and/or alkylnaphthalenes, and salts of sulfosuccinates and/or sulfosuccinamates. In some embodiments the ionic surfactant is an alkaline earth salt of an alkylaryl sulfonate. In some embodiments the ionic surfactant is calcium dodecylbenzene sulfonate which is available as Nansa® EVM 70/2E from Huntsman International LLC (The Woodlands, Tex.).

In some embodiments the fungicidal composition described herein may comprise, with respect to the composition, from about 1 gram per liter (g/L) to about 100 g/L, from about 5 g/L to about 100 g/L, from about 10 g/L to about 100 g/L, from about 20 g/L to about 100 g/L, from about 30 g/L to about 100 g/L, from about 30 g/L to about 90 g/L, from about 30 g/L to about 80 g/L, from about 40 g/L to about 70 g/L, from about 50 g/L to about 70 g/L, or from about 55 g/L to about 65 g/L of at least one of an ionic surfactant.

In some embodiments, the fungicidal composition described herein may include a surfactant that is a nonionic surfactant. Suitable nonionic surfactants for use with the fungicidal compositions described herein may include alkoxylates. N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with from 1 to 50 molar equivalents of an alkoxylating agent such as ethylene oxide (EO) and/or propylene oxide (PO).

In some embodiments the fungicidal composition described herein may include a nonionic surfactant that is an alkoxylate such as, for example, an alcohol initiated EO/PO block copolymer such as a butanol initiated EO/PO block copolymer, which may also be known as a polyalkylene glycol monobutyl ether, a poly(ethylene glycol-co-propylene glycol) monobutyl ether, or a propylene oxide ethylene oxide polymer monobutyl ether. In some embodiments the butanol initiated EO/PO block copolymer may have a degree of ethoxylation of from about 20 to about 30 and a degree of propoxylation of from about 20 to about 30. Suitable examples of these EO/PO block copolymers may include Toximul® 8320 available from Stepan (Northfield, Ill.), Termul® 5429 available from Huntsman International LLC (The Woodlands, Tex.), Tergitol™ XD available from Dow Chemical (Midland, Mich.), and Ethylan™ NS 500LQ available from AkzoNobel (Chicago, Ill.).

In some embodiments the fungicidal composition described herein may include a nonionic surfactant that is an alkoxylate such as, for example, an alcohol initiated EO/PO block copolymer like a 4-butoxy-1-butanol initiated EO/PO block copolymer (CAS number 99821-01-9) of which Atlas™ G5000 and Atlas™ G5002L are examples, and which are available from Croda (Edison, N.J.). In some embodiments the 4-butoxy-1-butanol initiated EO/PO block copolymer may have a degree of ethoxylation of from about 20 to about 30 and a degree of propoxylation of from about 20 to about 30.

In some embodiments the nonionic surfactant for use with the fungicidal composition described herein that is an alcohol initiated EO/PO block copolymer may provide improved active ingredient stability to the composition.

In some embodiments the fungicidal composition described herein may include a nonionic surfactant that is an alcohol ethoxylate such as a tridecyl alcohol ethoxylate, of which Synperonic™ 13/10, available from Croda (Edison, N.J.), is a suitable example which includes 10 EO units (degree of ethoxylation of 10).

In some embodiments the fungicidal composition described herein may include surfactants selected from the group consisting of at least one ionic surfactant that is an anionic surfactant and at least two non-ionic surfactants.

In some embodiments the fungicidal composition described herein may comprise, with respect to the composition, from about 1 gram per liter (g/L) to about 200 g/L, from about 10 g/L to about 190 g/L, from about 10 g/L to about 180 g/L, from about 20 g/L to about 160 g/L, from about 30 g/L to about 150 g/L, from about 40 g/L to about 140 g/L, from about 50 g/L to about 130 g/L, from about 60 g/L to about 120 g/L, from about 70 g/L to about 110 g/L, from about 80 g/L to about 100 g/L, or from about 85 g/L to about 95 g/L of at least one of a non-ionic surfactant.

C. WATER IMMISCIBLE ORGANIC SOLVENT

In certain embodiments, the described fungicidal composition includes a water immiscible organic solvent. "Water immiscible organic solvent" as defined herein means an organic solvent that has low water solubility and when mixed with an equivalent volume of water forms two discrete liquid layers. In some embodiments, the described fungicidal composition includes a water immiscible organic solvent that has a solubility in water of not greater than about 500 mg/L, about 600 mg/L, about 700 mg/L, about 800 mg/L, about 900 mg/L, or about 1000 mg/L. In some embodiments, the described composition includes a water immiscible organic solvent that has solubility in water of not greater than about 1250 mg/L, about 1500 mg/L, about 1750 mg/L, about 2000 mg/L, about 3000 mg/L, about 5000 mg/L, about 10,000 mg/L, about 20,000 mg/L, about 30,000 mg/L, about 40,000 mg/L, or about 50,000 mg/L.

In some embodiments, the water immiscible organic solvent serves as a liquid medium that dissolves the active and inert ingredients of the described fungicidal composition to form a stable solution (i.e., an emulsifiable concentrate) that forms a stable emulsion when added to water.

In some embodiments, the water immiscible organic solvent is comprised of a mixture of at least three organic compounds or classes of organic compounds. These organic compounds may be selected from the chemical classes of ester compounds, amide compounds, ketone compounds, and alcohol compounds. The organic compounds that make up the water immiscible organic solvent may be derived from natural sources such as vegetable, seed or animal oils, and/or from petrochemical sources.

In some embodiments, the fungicidal composition described herein includes a water immiscible organic solvent comprising of a mixture of organic compounds including at least one each of: an acetate ester, an N,N-dialkylcarboxamide, and at least one of a ketone and an alcohol.

In some embodiments, the fungicidal composition described herein includes a water immiscible organic solvent comprising of a mixture of organic compounds including at least one each of: an acetate ester and an N,N-dialkylcarboxamide.

Suitable organic compounds that may comprise the water immiscible organic solvent of the fungicidal composition described herein that are acetate esters may include compounds such as, for example, n-butyl acetate, iso-butyl acetate, n-pentyl acetate, iso-pentyl acetate, n-hexyl acetate, iso-hexyl acetate, cyclohexyl acetate, phenyl acetate, n-heptyl acetate, iso-heptyl acetate, cyclohexylmethyl acetate, benzyl acetate, or mixtures thereof. Benzyl acetate is available as Jeffsol AG-1705 from Huntsman (The Woodlands, Tex.).

In some embodiments, the described fungicidal composition may include, with respect to the composition, from about 50 g/L to about 700 g/L, from about 100 g/L to about 700 g/L, from about 150 g/L to about 700 g/L, from about 200 g/L to about 700 g/L, from about 250 g/L to about 700 g/L, from about 275 g/L to about 650 g/L, from about 300 g/L to about 600 g/L, from about 350 g/L to about 550 g/L, from about 375 g/L to about 550 g/L, from about 375 g/L to about 500 g/L, or from about 400 g/L to about 475 g/L of an acetate ester.

In some embodiments, suitable organic compounds that may comprise the water immiscible organic solvent of the described fungicidal composition may include benzyl acetate, cyclohexylmethyl acetate, phenyl acetate, or mixtures thereof.

In some embodiments, suitable organic compounds that may comprise the water immiscible organic solvent of the described fungicidal composition may include benzyl acetate.

Suitable organic compounds that may comprise the water immiscible organic solvent of the fungicidal composition described herein that are N,N-dialkylcarboxamides include the naturally derived fatty acid dimethylamides such as, e.g., N,N-dimethylcaprylamide (N,N-dimethyloctanamide), N,N-dimethylcapramide (N,N-dimethyldecanamide), and mixtures thereof, which may also be known as the N,N-dimethyl fatty acid amides and are available commercially as Agnique® AMD 810 and Agnique® AMD 10, from BASF Corp. (Florham Park, N.J.). Genegen® 4166. Genegen® 4231 and Genegen® 4296, from Clariant (Charlotte, N.C.), Hallcomid M-8-10 and Hallcomid M-10, from Stepan (Northfield, Ill.), and Armid DM10 and Armid DM810 from AkzoNobel (Chicago, Ill.). These products may also include small amounts of N,N-dimethylhexanamide and/or N,N-dimethyldodecanamide. Additional examples of naturally derived organic compounds that are N,N-dialkylcarboxamides include the morpholine amides of caprylic/capric fatty acids ($C_8/C_{10}$) which are commercially available as JEFFSOL® AG-1730 Solvent from Huntsman International LLC (The Woodlands, Tex.).

In some embodiments, the described fungicidal composition may include, with respect to the composition, from about 25 g/L to about 300 g/L, from about 25 g/L to about 300 g/L, from about 50 g/L to about 300 g/L, from about 75 g/L to about 300 g/L, from about 100 g/L to about 300 g/L, from about 125 g/L to about 300 g/L, from about 150 g/L to about 300 g/L, from about 175 g/L to about 300 g/L, from about 175 g/L to about 250 g/L, from about 175 g/L to about 200 g/L, from about 200 g/L to about 250 g/L, from about 225 g/L to about 300 g/L, from about 250 g/L to about 300 g/L, or from about 270 g/L to about 300 g/L of at least one N,N-dialkylcarboxamide.

In some embodiments, the described fungicidal composition may include one or more than one a N,N-dialkylcarboxamide selected from the group consisting of N,N-dimethylcaprylamide, N,N-dimethylcapramide, or mixtures thereof.

In some embodiments, suitable organic compounds that may comprise the water immiscible organic solvent of the fungicidal composition described herein that are at least one of a ketone and an alcohol may include compounds such as, acetophenone, cyclohexanone, ethyl isopropyl ketone, 2-heptanone, 2-hexanone, isophorone, methyl isobutyl ketone, 3-methyl-2-pentanone, 2-pentanone, 3-pentanone, trimethylcyclohexanone (dihydroisophorone), cyclohexanol, 2-heptanol, 2-ethylhexanol, and straight chain alcohols such as, for example, 1-hexanol, 1-heptanol, 1-octanol, 1-nonanol, 1-decanol, and the like, fatty alcohols such as oleyl alcohol and the like, and mixtures thereof.

In some embodiments, the described fungicidal composition may include, with respect to the composition, from about 25 g/L to about 150 g/L, from about 50 g/L to about 150 g/L, from about 50 g/L to about 125 g/L, from about 60 g/L to about 120 g/L, from about 70 g/L to about 120 g/L, from about 70 g/L to about 110 g/L, from about 70 g/L to about 100 g/L, or from about 70 g/L to about 90 g/L, of at least one of a ketone and an alcohol.

In some embodiments, the at least one of a ketone and an alcohol included in the described fungicidal composition may be selected from the group consisting of acetophenone, cyclohexanone, 2-ethylhexanol, 2-heptanol, and mixtures thereof.

In some embodiments, the at least one of a ketone and an alcohol included in the described fungicidal composition may be selected from the group consisting of acetophenone, cyclohexanone, and mixtures thereof.

In some embodiments, the at least one of a ketone and an alcohol included in the described fungicidal composition may be cyclohexanone.

In some embodiments, the at least one of a ketone and an alcohol included in the described fungicidal composition may provide improved solubility of Compound A in the described fungicidal composition.

In some embodiments, the at least one of a ketone and an alcohol included in the described fungicidal composition that is cyclohexanone, may provide improved solubility of Compound A in the described fungicidal composition.

In some embodiments, the water immiscible organic solvent may provide unexpected beneficial or synergistic effects to the described fungicidal composition such as, for example: (1) improved fungicidal performance of the composition when applied in spray applications to plants, (2) improved active ingredient solubility in the described compositions, and/or (3) improved Compound A chemical stability in the described composition during storage.

In some embodiments, the water immiscible organic solvent of the described fungicidal composition may provide unexpected beneficial or synergistic effects such as the formation of a stable, homogenous emulsifiable concentrate that readily emulsifies and forms a stable, oil-in-water emulsion without appreciable crystallization or precipitation of any of the ingredients when the composition is added to water.

In some embodiments, the water immiscible organic solvent of the fungicidal compositions described herein may include benzyl acetate, one or more than one of a fatty acid N,N-dimethylcarboxamide and cyclohexanone.

In some embodiments, the water immiscible organic solvent of the fungicidal compositions described herein may include benzyl acetate and one or more than one of a fatty acid N,N-dimethylcarboxamide.

The water immiscible organic solvent that may provide the unexpected beneficial or synergistic effects to the fungicidal composition described herein may depend on the selection of and/or the relative ratios of the organic compounds that comprise the water immiscible organic solvent.

In some embodiments, the ratio of the organic compounds included in the water immiscible organic solvent of the fungicidal composition described herein may range, on a weight basis, from about 1-10:1-10:1-10 of the acetate ester:the one or more than one of the fatty acid N,N-dimethylcarboxamide:the at least one of a ketone and an alcohol. In some embodiments, the ratio of the organic compounds may range from about 1-8:1-5:1-5, from about 1-6:1-3:1-2, from about 2-6:1-3:1-2, from about 3-6:1-3:1-2, from about 4-6:1-3:1-2, from about 4-5:1.5-2.5:0.5-1.5, or from about 4.5-5:1.8-2.2:0.8-1.2 of the acetate ester:the one or more than one of the fatty acid N,N-dimethylcarboxamide:the at least one of a ketone and an alcohol, on a weight basis.

In some embodiments, the ratio of the organic compounds included in the water immiscible organic solvent of the fungicidal composition described herein may range, on a weight basis, from about 4-6:1-3:1-2, from about 4-5:1.5-2.5:0.7-1.2, or from about 4.5-5:1.9-2.3:0.8-1.1, of benzyl acetate:the one or more than one of a fatty acid N,N-dimethylcarboxamide:cyclohexanone.

In some embodiments, the ratio of the organic compounds included in the water immiscible organic solvent of the fungicidal composition described herein may range, on a weight basis, from about 1-10:1-10 of the acetate ester:the one or more than one of the fatty acid N,N-dimethylcarboxamide. In some embodiments, the ratio of the organic compounds in the water immiscible organic solvent may range from about 1-5:1-5, from about 1-5:1-2, from about 1-4:1-2, from about 1-3:1-2, from about 1-3:1, from about 4:1, from about 3:1, from about 2:1, or from about 1:1 of benzyl acetate:the one or more than one of a fatty acid N,N-dimethylcarboxamide.

In some embodiments, the described fungicidal composition exhibits beneficial or synergistic properties related to the composition of the water immiscible organic solvent such as improved fungicidal efficacy after spray application of the composition to vegetation or an area adjacent thereto to prevent the growth of fungal pathogens or diseases.

In some embodiments, the described fungicidal composition exhibits beneficial or synergistic properties related to the composition of the water immiscible organic solvent such as improved fungicidal control of *Septoria tritici* (SEPTTR; wheat leaf blotch) and *Puccinia triticina* (PUCRT; wheat brown rust) after spray application of the composition to vegetation or an area adjacent thereto to prevent the growth of the fungal pathogens or diseases.

In some embodiments, the described fungicidal composition exhibits beneficial or synergistic properties related to the composition of the water immiscible organic solvent such as improved active ingredient chemical stability during storage.

In some embodiments, the described fungicidal composition exhibits beneficial or synergistic properties related to the composition of the water immiscible organic solvent such as improved active ingredient solubility in the composition.

D. ADDITIONAL FUNGICIDAL COMPOUND

In certain embodiments, the described fungicidal composition may include at least one additional fungicidal compound. Suitable at least one additional fungicidal compounds may include, for example, azoxystrobin, bifujunzhi, coumethoxystrobin, coumoxystrobin, dimoxystrobin, enestroburin, enoxastrobin, fenaminstrobin, fenoxystrobin, flufenoxystrobin, fluoxastrobin, jiaxiangjunzhi, kresoximmethyl, mandestrobin, metominostrobin, orysastrobin, picoxystrobin, pyraclostrobin, pyrametostrobin, pyraoxystrobin, triclopyricarb, trifloxystrobin, methyl 2-[2-(2,5-dimethylphenyloxymethyl)phenyl]-3-methoxyacrylate, pyribencarb, triclopyricarb/chlorodincarb, famoxadon, fenamidon, cyazofamid, amisulbrom, benodanil, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthio-biphenyl-2-yl)-3-difluoromethyl-1-methyl-1H-pyrazole-4-carboxamide, N-(2-(1,3,3-trimethylbutyl)phenyl)-1,3-dimethyl-5-fluoro-1H-pyrazole-4-carboxamide, N-[9-(dichloromethylene)-1,2,3,4-tetrahydro-1,4-methanonaphthalen-5-yl]-3-(difluoromethyl)-1-methyl-1H-pyrazole-4-carboxamide, diflumetorim, binapacryl, dinobuton, dinocap, meptyl-dinocap, fluazinam, ferimzone, ametoctradin, silthiofam, azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, imazalil, pefurazoate, prochloraz, triflumizole, pyrimidines, fenarimol, nuarimol, pyrifenox, triforine, aldimorph, dodemorph, dodemorph acetate, fenpropimorph, tridemorph, fenpropidin, piperalin, spiroxamine, fenhexamid, benalaxyl, benalaxyl-M, kiralaxyl, metalaxyl, metalaxyl-M (mefenoxam), ofurace, oxadixyl, hymexazole, octhilinone, oxolinic acid, bupirimate, benomyl, carbendazim, fuberidazole, thiabendazole, thiophanate-methyl, 5-chloro-7-(4-methyl-piperidin-1-yl)-6-(2,4,6-trifluorophenyl)-[1,2,4]triazolo[1,5-a]pyrimidine, diethofencarb, ethaboxam, pencycuron, fluopicolid, zoxamid, metrafenon, pyriofenon, cyprodinil, mepanipyrim, pyrimethanil, fluoroimide, iprodione, procymidone, vinclozolin, fenpiclonil, fludioxonil, quinoxyfen, edifenphos, iprobenfos, pyrazophos, isoprothiolane, dicloran, quintozene, tecnazene, tolclofos-methyl, biphenyl, chloroneb, etridiazole, dimethomorph, flumorph, mandipropamid, pyrimorph, benthiavalicarb, iprovalicarb, valifenalate and 4-fluorophenyl N-(1-(1-(4-cyanophenyl)ethanesulfonyl)but-2-yl)carbamate, propamocarb, propamocarb hydrochloride, ferbam, mancozeb, maneb, metiram, propineb, thiram, zineb, ziram, anilazine, chlorothalonil, captafol, captan, folpet, dichlofluanid, dichlorophen, flusulfamide, hexachlorobenzene, pentachlorophenol, phthalid, tolylfluanid, N-(4-chloro-2-nitrophenyl)-N-ethyl-4-methylbenzenesulfonamide, guanidine, dithianon, validamycin, polyoxin B, pyroquilon, tricyclazole, carpropamid, dicyclomet, fenoxanil, and mixtures thereof.

In some embodiments, the described composition may include at least one additional fungicidal compound selected from azoxystrobin, bifujunzhi, coumethoxystrobin, coumoxystrobin, dimoxystrobin, enestroburin, enoxastrobin, fenaminstrobin, fenoxystrobin, flufenoxystrobin, fluoxastrobin, jiaxiangjunzhi, kresoxim-methyl, mandestrobin, metominostrobin, orysastrobin, picoxystrobin, pyraclostrobin, pyrametostrobin, pyraoxystrobin, triclopyricarb, trifloxystrobin, methyl 2-[2-(2,5-dimethylphenyloxymethyl)phenyl]-3-methoxyacrylate, azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, imazalil, pefurazoate, prochloraz, triflumizole, pyrimidines, fenarimol, nuarimol, pyrifenox, triforine, and mixtures thereof.

In some embodiments, the described composition may include at least one additional fungicidal compound selected from benodanil, bixafen, boscalid, carboxin, fenfuram, fluopyram, flutolanil, fluxapyroxad, furametpyr, isopyrazam, mepronil, oxycarboxin, penflufen, penthiopyrad, sedaxane, thifluzamide, and mixtures thereof.

In some embodiments, the described composition may include at least one additional fungicidal compound selected from azoxystrobin, kresoxim-methyl, picoxystrobin, pyraclostrobin, trifloxystrobin, epoxiconazole, fenbuconazole, myclobutanil, propiconazole, prothioconazole, tebuconazole, and mixtures thereof.

In some embodiments, the described fungicidal composition may include the fungicidal compound pyraclostrobin.

In some embodiments, the described fungicidal composition may include the fungicidal compound prothioconazole.

In some embodiments, the described fungicidal composition may include the fungicidal compound propiconazole.

In some embodiments, the described fungicidal composition that includes at least one additional fungicidal compound may show synergistic fungicidal activity.

In some embodiments the fungicidal composition described herein may comprise, with respect to the composition, from about 1 gram active ingredient per liter (g ai/L) to about 200 g ai/L, from about 5 g ai/L to about 175 g ai/L, from about 10 g ai/L to about 150 g ai/L, from about 20 g ai/L to about 150 g ai/L, from about 20 g ai/L to about 125 g ai/L, from about 20 g ai/L to about 100 g ai/L, from about 20 g ai/L to about 90 g ai/L, from about 30 g ai/L to about 90 g ai/L, from about 40 g ai/L to about 90 g ai/L, from about 40 g ai/L to about 80 g ai/L, from about 45 g ai/L to about 75 g ai/L, or from about 45 g ai/L to about 70 g ai/L of the at least one additional fungicidal compound. The fungicidal composition described herein may also comprise from about from about 30 g ai/L to about 150 g ai/L, from about 40 g ai/L to about 150 g ai/L, from about 50 g ai/L to about 150 g ai/L, from about 60 g ai/L to about 150 g ai/L, from about 70 g ai/L to about 150 g ai/L, from about 80 g ai/L to about 150 g ai/L, from about 90 g ai/L to about 150 g ai/L, from about 100 g ai/L to about 150 g ai/L, from about 110 g ai/L to about 150 g ai/L, from about 120 g ai/L to about 150 g ai/L, from about 125 g ai/L to about 140 g ai/L, or from about 125 g ai/L to about 135 g ai/L of the at least one additional fungicidal compound.

E. ADJUVANTS

Adjuvants are compounds which have negligible or even no pesticidal activity themselves, and which improve the biological performance of a pesticidal composition on one or more target pests. Examples of such adjuvants may include surfactants such as alcohol ethoxylates, alkyl naphthalene sulphonates, alkyl phosphonates, alkylbenzene sulphonates, benzyldimethylcocalkyl ammonium salts, sorbitan ester ethoxylates, and modified organosilicones; also, mineral or vegetable oils, and other auxilaries. Further examples of adjuvants are listed by Knowles in, "Adjuvants and Additives," Agrow Reports DS256, T&F Informa UK, 2006, Chapter 5.

In some embodiments, the fungicidal composition described herein may include an adjuvant to improve fungicidal performance.

In some embodiments, the fungicidal composition described herein may include an adjuvant to improve fungicidal performance selected from the class of modified organosilicone surfactants such as, for example, the polyether modified organopolysiloxanes such as Breakthru® S233, which is available from Evonik Industries (Parsippany, N.J.).

In some embodiments, the fungicidal composition described herein may include an adjuvant to improve fungicidal performance selected from the class of alkyl phosphonate adjuvants such as, for example, bis (2-ethylhexyl) 2-ethylhexylphosphonate (also known as BEEP), which is available from Rhodia (Cranberry, N.J.).

In some embodiments, non-ionic surfactants such as, for example, a tridecyl alcohol ethoxylate (i.e., Synperonic™ 13/10) may serve as an adjuvant that improves the fungicidal performance of the fungicidal composition described herein.

In some embodiments, the fungicidal composition described herein may include, with respect to the composition, from about 1 g/L to about 200 g/L of one or more adjuvants used to improve fungicidal performance. In some embodiments, the fungicidal composition may include from about 1 g/L to about 150 g/L, from about 5 g/L to about 150 g/L, from about 10 g/L to about 150 g/L, from about 20 g/L to about 150 g/L, from about 25 g/L to about 140 g/L, from about 30 g/L to about 130 g/L, from about 35 g/L to about 125 g/L, from about 40 g/L to about 120 g/L, from about 40 g/L to about 110 g/L, from about 40 g/L to about 100 g/L, from about 40 g/L to about 90 g/L, from about 40 g/L to about 80 g/L, from about 40 g/L to about 70 g/L, from about 50 g/L to about 70 g/L, from about 40 g/L to about 130 g/L, from about 50 g/L to about 120 g/L, from about 60 g/L to about 120 g/L, from about 70 g/L to about 120 g/L, from about 80 g/L to about 120 g/L, from about 90 g/L to about 120 g/L, or from about 100 g/L to about 120 g/L, of one or more adjuvants used to improve fungicidal performance.

F. STORAGE STABILITY

As used herein, stable compositions are compositions that are stable physically and/or chemically for defined periods of time to the environments in which they are produced, transported and/or stored. Aspects of stable compositions include, but are not limited to: physical stability at temperatures that range from about 0° C. to about 54° C., homogeneity, pourability, liquids that form little or no precipitated solids or crystals or exhibit little or no phase separation, compositions that readily emulsify when poured into a spray tank of water and retain their biological efficacy when applied, for example, by spray application to target pests.

In some embodiments, the described composition forms a stable, homogeneous emulsifiable concentrate that does not exhibit appreciable phase separation under the storage conditions. In some embodiments, the described composition exhibits very little change in viscosity under the storage conditions. In some embodiments, the described composition exhibits very little chemical decomposition of the active ingredient or active ingredients under the storage conditions.

In some embodiments, the described fungicidal composition is stable at temperatures of greater than or equal to about 25° C. for a period of at least 2, 4, 6 or 8 weeks. In some embodiments, the described composition is stable at temperatures of greater than or equal to about 40° C. for a period of at least 2, 4, 6 or 8 weeks. In some embodiments, the described composition is stable at temperatures of greater than or equal to about 54° C. for a period of at least about 2 weeks.

In some embodiments, the described fungicidal composition does not exhibit or does not significantly exhibit separation, precipitation or crystallization of any of the components at low temperatures. In some embodiments, the described fungicidal composition remains as a homogeneous emulsifiable concentrate after storage for at least about 2 weeks at temperatures below about 20° C., below about 10° C., or equal to or less than about 5° C., or equal to or less than about 0° C. or equal to or less than about −5° C. or equal to or less than about −10° C. In certain embodiments, the compositions are stable at these temperatures for at least about 2, 4, 6, or 8 weeks.

In some embodiments, the described fungicidal composition remains as a homogeneous concentrate after subjecting it to freeze/thaw (F/T) conditions for at least about 2 or 4 weeks where the temperature is cycled from about −10° C. to about 40° C. every 24 hours.

In some embodiments, the storage stability of the described fungicidal composition may be dependent on one or more ingredients and their concentration in the composition. Such ingredients may include, but are not limited to, the organic compounds that comprise the water immiscible organic solvent, the nonionic surfactant, the at least one additional fungicidal compound, dialkylamines such as dimethylamine that are present in or formed from the N,N-dialkylcarboxamides, and water.

In some embodiments, the chemical stability of the active ingredient or active ingredients in the described fungicidal composition may be improved by including a ketone or an alcohol in the composition.

In some embodiments, the chemical stability of the active ingredient or active ingredients in the described fungicidal composition may be improved by including a nonionic surfactant in the composition.

In some embodiments, the chemical stability of the active ingredient or active ingredients in the described fungicidal composition may be improved by eliminating or reducing the amount of a dialkylamine in the composition.

In some embodiments, the chemical stability of the active ingredient or active ingredients in the described fungicidal composition may be improved by eliminating or reducing the amount of water in the composition.

In some embodiments, the chemical stability of the first active ingredient in the described fungicidal composition may be reduced by adding at least one additional fungicidal compound to the composition.

G. METHODS OF PREPARATION AND USE

Also described herein is a process or method for the preparation of the described fungicidal composition which includes mixing together the one or more fungicide active ingredients, the inert ingredients and the water immiscible organic solvent to form a stable, homogenous, emulsifiable concentrate that readily emulsifies to form a stable, homogeneous, emulsion when added to water.

In some embodiments, the fungicidal composition (emulsifiable concentrate) described herein may be prepared by the steps of:

(1) preparing a solution of the first fungicidal compound in the water immiscible organic solvent;

(2) adding one or more surfactants to the solution prepared in step (1) to form a solution:

(3) optionally, adding at least one additional fungicidal compound to the solution prepared in step (2); and (4) optionally, adding any additional compatible active or inert ingredients to the solution prepared in step (3) to from a solution.

The described fungicidal composition may also be prepared by changing the relative order of the steps, or adding or eliminating steps to the preparation described herein as may be readily determined by one of ordinary skill in the art.

The disclosure furthermore relates to an emulsion obtainable (preferably obtained) by mixing water with the emulsifiable concentrate described herein. The emulsion normally arises spontaneously upon mixing. In most cases, the emulsion is an oil-in-water emulsion. The mixing ratio of water to concentrate may be in the range of from 1000 to 1 up to 1 to 1, preferably 200 to 1 up to 3 to 1.

Also provided herein is a method of controlling plant derived fungal pathogens or diseases comprising contacting the vegetation or an area adjacent thereto to prevent the growth of the fungal pathogens or diseases a fungicidally effective amount of a fungicidal composition comprising:

a) a fungicidal compound of the Formula

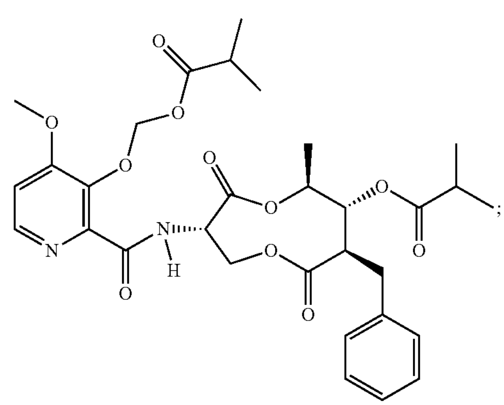 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

;

b) at least one ionic surfactant;

c) at least one nonionic surfactant;

d) an acetate ester;

e) an N,N-dialkylcarboxamide; and f) optionally, at least one of a ketone and an alcohol.

Plant fungal pathogens that may be controlled by the described fungicidal compositions include *Septoria tritici, Puccinia triticina, Mycosphaerella graminicola, Puccinia triticina, Puccinia striiformis, Venturia inaequalis, Ustilago maydis, Uncinula necator, Rhynchosporium secalis, Leptosphaeria nodorum, Magnaporthe grisea, Monilinia fructicola, Pseudoperonospora cubensis, Pseudocercosporella herpotrichoides, Phakopsora pachyrhizi, Phaeosphaeria nodorum, Blumeria graminis tritici, Blumeria graminis hordei, Erysiphe cichoracearum, Ezysiphe graaminis, Glomerella lagenarium, Cercospora beticola, Alternaria solani, Rhizoctonia solani, Plasmopara viticola, Phytophthora infestans, Pyricularia oryzae*, and *Pyrenophora teres*.

Plant fungal diseases that may be controlled by the described fungicidal compositions include anthracnose, blasts, *botrytis*, brown rust, blister smut, brown rot, downy mildew, *fusarium*, powdery mildew, rusts, glume blotch, leaf blotch, net blotch, sheath blight, stripe rust, scab, eye spot, leaf spot, early blight, and late blight.

In some embodiments, the described fungicidal composition, after spray application to plant surfaces, exhibits rainfast properties by offering good fungicidal efficacy after exposure to rain or other moisture causing events.

This described method includes use of the described fungicidal composition for protecting a plant against attack by a phytopathogenic organism or the treatment of a plant already infested by a phytopathogenic organism, comprising the step of applying the described fungicidal composition, to soil, a plant, a part of a plant, foliage, flowers, fruit, and/or seeds, or any surface adjacent to a plant in a disease inhibiting and phytologically acceptable amount. The term "disease inhibiting and phytologically acceptable amount" refers to an amount of a compound that kills or inhibits the plant disease for which control is desired, in an amount not significantly toxic to the plant being treated. The exact concentration of active compound required varies with the fungal disease to be controlled, the type of formulations employed, the method of application, the particular plant species, climate conditions, and the like, as is well known in the art.

The fungicidal compositions described herein may optionally be diluted in an aqueous spray mixture for agricultural application such as for the control of phytopathogenic fungi in crop fields. Such compositions are typically diluted with an inert carrier, such as water, before application. The diluted compositions, which are usually applied, for example, to crops, the locus of crops or the locus of where phytopathogenic fungi may eventually emerge, in some embodiments include about 0.0001 to about 1 weight percent of the active ingredient or from 0.001 to about 1 weight percent of the active ingredient. The present compositions can be applied, for example, to crop plants or their locus by the use of conventional ground or aerial sprayers, and by other conventional means known to those skilled in the art.

H. OPTIONAL INGREDIENTS

The compositions disclosed herein may optionally include inert formulation ingredients such as, but not limited to, dispersants, surfactants and wetting agents. These optional inert ingredients may include surfactants conventionally used in the art of formulation that are described, inter alia, in "McCutcheon's Detergents and Emulsifiers Annual," MC Publishing Corp., Ridgewood, N.J., 1998 and in the "Encyclopedia of Surfactants," Vol. I-III, Chemical Publishing Co., New York, 1980-81. These surface-active agents can be anionic, cationic or nonionic in character and can be employed as emulsifying agents, wetting agents, suspending agents, or for other purposes.

In addition to the specific methods and compositions set forth above, the methods and compositions described herein also may include compositions comprising one or more additional compatible ingredients. These additional ingredients may include, for example, one or more pesticides or other ingredients, which may be dissolved or dispersed in the composition and may be selected from acaricides, algicides, antifeedants, avicides, bactericides, bird repellents, chemosterilants, defoliants, desiccants, disinfectants, fungicides, herbicide safeners, herbicides, insect attractants, insecticides, insect repellents, mammal repellents, mating disrupters, molluscicides, nematicides, plant activators, plant growth regulators, rodenticides, semiochemicals, synergists, and virucides. Also, any other additional ingredients providing functional utility such as, for example, antifoam agents, antimicrobial agents, buffers, corrosion inhibitors, dispersing agents, dyes, fragrants, freezing point depressants, neutralizing agents, odorants, penetration aids, sequestering agents, spray drift control agents, spreading agents, stabilizers, sticking agents, viscosity-modifying additives, water soluble solvents and the like, may be included in these compositions.

When the described compositions are used in combination with the additional active ingredients such as, for example, insecticide active ingredients, the compositions described herein can be formulated with the other active ingredient or active ingredients as premix concentrates, tank-mixed in water with the other active ingredient or active ingredients for spray application, or applied sequentially with the other active ingredient or active ingredients in separate spray applications.

The compositions and methods described herein may be used in controlling fungal diseases in crops possessing single, multiple or stacked genomic traits conferring tolerance to one or more herbicide chemistries and/or inhibitors with single or multiple modes of action.

I. EXAMPLES

The following Examples are presented to illustrate various aspects of the compositions described herein and should not be construed as limitations to the claims.

Example 1

Preparation of Representative Samples of the Described Fungicidal Composition

TABLE 1

Fungicidal Compositions Described Herein

| Ingredient | Role | Amount (g/L) |
|---|---|---|
| 1st fungicide cmpd. | active ingredient | 1-250 |
| 2nd fungicide cmpd. | active ingredient | 0-200 |
| surfactant | emulsifier | 1-100 |
| surfactant | emulsifier | 1-100 |
| surfactant | emulsifier | 1-100 |
| organosilicone | adjuvant | 10-100 |
| ketone | solvent | 0-500 |

TABLE 1-continued

Fungicidal Compositions Described Herein

| Ingredient | Role | Amount (g/L) |
|---|---|---|
| acetate ester | solvent | 10-750 |
| N,N-dialkylcarboxamide[1] | solvent | 10-500 |
| polydimethylsiloxane | antifoam | 0.01-1 |

[1] Also known as an N,N-dimethyl fatty acid amide.

Sample 1:

An emulsion concentrate comprising Compound A as the active ingredient was prepared using the ingredients in Table 2 and as described in the steps below (indicated values are g per 100 mL formulation):

TABLE 2

| Sample 1 Fungicidal Composition | | |
|---|---|---|
| 1st fungicide cmpd | Compound A, 85% tech. | 5.88 |
| surfactant | Nansa EVM 70/2E | 6.00 |
| surfactant | Toximul 8320 | 4.50 |
| surfactant | Synperonic 13/10 | 4.50 |
| organosilicone | Breakthru S233 | 5.00 |
| ketone | cyclohexanone | 9.89 |
| acetate ester | benzyl acetate | 46.81 |
| N,N-dialkylcarboxamide | Hallcomid M-8-10 | 19.03 |
| polydimethylsiloxane | SAG 1572 | 0.01 |

(1) An active ingredient premix of cyclohexanone, benzyl acetate, Hallcomid M-8-10 and Compound A was prepared.
(2) The premix from (1) was warmed to 35-40° C. and stirred until a clear solution was obtained.
(3) The remaining ingredients were added to the premix followed by mixing until a uniform composition was obtained.

Sample 2:

An emulsion concentrate comprising Compound A and prothioconazole active ingredients was prepared using the ingredients in Table 3 and as described in the steps below (indicated values are g per 100 mL formulation):

TABLE 3

| Sample 2 Fungicidal Composition | | |
|---|---|---|
| 1st fungicide cmpd | Compound A, 85% technical | 5.88 |
| 2nd fungicide cmpd | prothioconazole 96% tech. | 10.42 |
| surfactant | Nansa EVM 70/2E | 6.00 |
| surfactant | Toximul 8320 | 4.50 |
| surfactant | Synperonic 13/10 | 4.50 |
| organosilicone | Breakthru S233 | 5.00 |
| ketone | Cyclohexanone | 8.90 |
| acetate ester | Benzyl acetate | 42.11 |
| N,N-dialkylcarboxamide | Hallcomid M-8-10 | 17.11 |
| polydimethylsiloxane | SAG 1572 | 0.01 |

(1) An active ingredient premix of cyclohexanone, benzyl acetate, Hallcomid M-8-10, prothioconazole and Compound A was prepared.
(2) The premix from (1) was stirred until a clear solution was obtained.
(3) The remaining ingredients were added to the premix followed by mixing until a uniform composition was obtained.

Sample 3:

An emulsion concentrate comprising Compound A and pyraclostrobin active ingredients was prepared using the ingredients in Table 4 and as described in the steps below (indicated values are g per 100 mL formulation):

TABLE 4

| Sample 3 Fungicidal Composition | | |
|---|---|---|
| 1st fungicide cmpd | Compound A, 85% technical | 5.88 |
| 2nd fungicide cmpd | pyraclostrobin 98% tech. | 6.38 |
| surfactant | Nansa EVM 70/2E | 6.00 |
| surfactant | Toximul 8320 | 4.50 |
| surfactant | Synperonic 13/10 | 4.50 |
| organosilicone | Breakthru S233 | 5.00 |
| ketone | Cyclohexanone | 9.29 |
| acetate ester | Benzyl acetate | 43.82 |
| N,N-dialkylcarboxamide | Hallcomid M-8-10 | 17.86 |
| polydimethylsiloxane | SAG 1572 | 0.01 |

(1) A solvent premix of cyclohexanone, benzyl acetate and Hallcomid M-8-10 was prepared.
(2) The premix from (1) was stirred until a clear solution was obtained.
(3) The surfactants, adjuvant and antifoaming agent are added to the premix followed by mixing until a uniform composition was obtained.
(4) The pyraclostrobin technical active ingredient was heated until molten (70° C.) and then added to the premix prepared in step (3) whilst mixing.
(5) The Compound A technical active ingredient was added to the premix followed by mixing until a uniform composition was obtained.

Sample 4:

An emulsion concentrate comprising Compound A and prothioconazole active ingredients was prepared using the ingredients in Table 5 and as described in the steps below (indicated values are g per 100 mL formulation):

TABLE 5

| Sample 4 Fungicidal Composition | | |
|---|---|---|
| 1st fungicide cmpd | Compound A, 85% tech. | 7.85 |
| 2nd fungicide cmpd | prothioconazole, 98% tech. | 13.89 |
| surfactant | Nansa EVM 70/2E | 6.00 |
| surfactant | Toximul 8320 | 4.50 |
| surfactant | Synperonic 13/10 | 4.50 |
| organosilicone | Breakthru S233 | 5.00 |
| ketone | Cyclohexanone | 6.67 |
| acetate ester | Benzyl acetate | 38.71 |
| N,N-dialkylcarboxamide | Hallcomid M-8-10 | 15.72 |
| polydimethylsiloxane | SAG 1572 | 0.01 |

(1) A solvent premix of cyclohexanone, benzyl acetate and Hallcomid M-8-10 was prepared.
(2) The premix from (1) was stirred until a clear solution was obtained.
(3) The surfactants, adjuvant and antifoaming agent were added to the premix followed by mixing until a uniform composition was obtained.
(4) The prothioconazole and Compound A technical active ingredients were added to the premix followed by mixing until a uniform composition was obtained.

Sample 5:

An emulsion concentrate comprising Compound A and pyraclostrobin active ingredients was prepared using the ingredients and amounts listed in Table 6 in a manner similar to that described for Sample 3 (indicated values are g per 1 L formulation):

TABLE 6

| Sample 5 Fungicidal Composition | | |
|---|---|---|
| 1st fungicide cmpd | Compound A, 85% tech. | 66.7 g/L |
| 2nd fungicide cmpd | pyraclostrobin 98% tech. | 83.3 |
| surfactant | Nansa EVM 70/2E | 60 |
| surfactant | Toximul 8320 | 45 |
| surfactant | Synperonic 13/10 | 45 |
| organosilicone | Breakthru S233 | 66.7 |
| ketone | Cyclohexanone | 86.9 |
| acetate ester | Benzyl acetate | 410.2 |
| N,N-dialkylcarboxamide | Hallcomid M-8-10 | 181.2 |
| polydimethylsiloxane | SAG 1572 | 0.1 |

Sample 6:

An emulsion concentrate comprising Compound A and prothioconazole active ingredients was prepared using the ingredients and amounts listed in Table 7 in a manner similar to that described for Sample 3 (indicated values are in grams per 100 mL formulation):

TABLE 7

| Sample 6 Fungicidal Composition | | |
| --- | --- | --- |
| 1st fungicide cmpd | Compound A, 84% technical | 5.95 |
| 2nd fungicide cmpd | prothioconazole 96% tech. | 7.81 |
| surfactant | Nansa EVM 70/2E | 7.50 |
| surfactant | Toximul 8320 | 3.00 |
| surfactant | Synperonic 13/10 | 4.50 |
| acetate ester | Benzyl acetate | 48.1 |
| N,N-dialkylcarboxamide | Hallcomid M-8-10 | 25.9 |

Sample 7:

An emulsion concentrate comprising Compound A and prothioconazole active ingredients was prepared using the ingredients and amounts listed in Table 8 in a manner similar to that described for Sample 3 (indicated values are in grams):

TABLE 8

| Sample 7 Fungicidal Composition | | |
| --- | --- | --- |
| 1st fungicide cmpd | Compound A, 84% technical | 1.15 |
| 2nd fungicide cmpd | prothioconazole 96% tech. | 1.51 |
| surfactant | Nansa EVM 70/2E | 1.49 |
| surfactant | Toximul 8320 | 0.60 |
| surfactant | Synperonic 13/10 | 0.89 |
| organosilicone | Breakthru S233 | 2.42 |
| acetate ester | Benzyl acetate | 8.95 |
| N,N-dialkylcarboxamide | Hallcomid M-8-10 | 2.98 |

Example 2

Solubility of Fungicidal Active Ingredients in Organic Solvents a) Relative Solubility of Compound A and Prothioconazole in Organic Solvents with Low Solubility in Water.

To prepare an effective EC composition comprising Compound A and prothioconazole the following solvent attributes must be achieved:

Compound A solubility needs to be above 10 wt % prothioconazole solubility needs to be above 20 wt % water solubility of solvent candidates should be below about 5 g/L or 0.5% so that good emulsion stability will be achieved when the EC is added to water Test Method: The approximate solubility of Compound A was determined by mixing a known mass of the active ingredient with an increasing mass of each solvent at ambient temperature. For example, 0.2 g of Compound A was mixed with 1.38 g of cyclohexanone giving a clear solution comprising 12.6% w/w Compound A. Cyclohexanone was therefore classified as a very good solvent for Compound A as it offered "High" solubility (see following table) and was included for further evaluation. The solubility of Compound A in the solvents used in this screening procedure was generally classified within the following concentration ranges:

| Compound A Solubility (wt %) | Relative Solubility |
| --- | --- |
| >8.4 | High |
| 8.4 to 5.6 | Medium |
| 5.6 to 3.0 | Low |
| <3.0 | Vely Low |

| Prothioconazole Solubility (wt %) | Relative Solubility |
| --- | --- |
| >30 | High |
| >20 to 30 | Medium |
| 10 to 20 | Low |
| <10 | Very Low |

Table 9 shows the relative solubility of Compound A and prothioconazole in a variety of organic solvents.

TABLE 9

Relative Solubility of Compound A and Prothioconazole in Organic Solvents at Ambient Temperature

| Solvent | Relative Solubility of Compound A | Relative Solubility of Prothioconazole | Solubility of Solvent in Water (g/L)[1] |
| --- | --- | --- | --- |
| Cyclohexanone | High | High | 8.6-25 |
| Methyl-5-(Dimethylamino)-2-Methyl-5-Oxopentanoate | High | High | 79 |
| Benzyl alcohol | High | Medium | 43 |
| N-formyl morpholine and propylene carbonate | High | Medium | Miscible[2] |
| Benzyl acetate | High | Low | 1.0-3.1 |
| Sulfolane | High | Low | 379 |
| Methyl salicylate | High | Very Low | <5 |
| Butyl benzoate | Medium | Low | $1.7e^{-4}$ |
| 2-heptanone | Medium | Low | 4.28 |
| Pentanedioic acid, 2-methyl-1,5-dimethyl ester | Medium | Low | 25 |
| Butyl lactate | Medium | Low | 42 |
| Isopropyl benzoate | Medium | Very Low | 0.64 |
| N,N dimethyl fatty acid amides | Low | High | 1.9-5.3 |
| Tributoxyethyl phosphate | Low | High | Miscible |
| Diethylene glycol monoethyl ether | Low | High | Miscible |

TABLE 9-continued

Relative Solubility of Compound A and
Prothioconazole in Organic Solvents at Ambient Temperature

| Solvent | Relative Solubility of Compound A | Relative Solubility of Prothioconazole | Solubility of Solvent in Water (g/L)[1] |
|---|---|---|---|
| dimethyl esters of adipic, glutaric and succinic acids | Low | Low | 53 |
| Ethyl Diglycol Acetate | Low | Very Low | Miscible |
| 2-ethylhexyl lactate[3] | Very Low | Medium | 1.9 |
| Polyethylene glycol | Very Low | Medium | Miscible |
| Polypropylene glycol | Very Low | Low | Miscible |
| 2-ethylhexanol | Very Low | Very Low | 0.88 |
| Methyl oleate | Very Low | Very Low | 0.0011 |
| Isoparaffin | Very Low | Very Low | <5 |
| Alkyl naphthalene mixture | Very Low | Very Low | <5 |
| Butylene carbonate | Very Low | Very Low | 7 |
| Soybean oil | Very Low | Very Low | <5 |
| Propylene carbonate | Very Low | Very Low | 17.5 |
| 2-ethylhexyl benzoate | Very Low | Very Low | 0.0004 |
| Di-n-butyl carbonate | Very Low | Very Low | 0.82 |

[1]Estimated from a survey of the literature;
[2]miscible means totally soluble in water in all amounts;
[3]2-ethylhexyl lactate/Compound A mixture freezes at 0° C.

b) Solubility of Compound A and Prothioconazole in Benzyl Acetate/AMD810 Blends at 10° C.

A study of the Compound A and prothioconazole solubility in blends of benzyl acetate/AMD810 was conducted. To each solvent blend both actives were added until each was saturated and the resulting mixtures were then stored at 10° C. until equilibrium was obtained. Aliquots of the supernatant layer were taken from each sample, filtered (0.45 μm mesh) and analyzed by HPLC to determine the solution concentration of each active in the blends. Table 10 shows the results.

TABLE 10

Solubility of a Mixture of Compound A and
Prothioconazole in Benzyl Acetate-AMD810 Blends at 10° C.

| Proportion of Benzyl acetate to AMD810 in Blend (wt %) | Prothioconazole Solubility at 10° C. (% w/w) | Compound A Solubility at 10° C. (% w/w) |
|---|---|---|
| 0 | 31.3 | 3.3 |
| 20 | 32.3 | 4.3 |
| 40 | 33.1 | 6.5 |
| 60 | 32.1 | 11.0 |
| 80 | 26.6 | 12.0 |
| 100 | 16.2 | 14.3 | c) Solubility of Compound A and Prothioconazole in Benzyl Acetate/AMD810/Cyclohexanone Blends at 10° C.

The weight fraction of each solvent was tested at a variety of levels (from 0 to 1) in the various blends shown in Table 11. A total of 20 g of each solvent blend was prepared per sample. For example, one of the blends (Blend 4) was prepared by combining cyclohexanone 0.2 (4 g), benzyl acetate 0.2 (4 g) and AMD810 0.6 (12 g). To Blend 4 were added amounts of Compound A and prothioconazole technical active ingredients to achieve saturation concentrations of each. The samples were then stored at 10° C. for one week and then were analysed for soluble active ingredient content. The results are shown in Table 11.

TABLE 11

Solubility of Compound A and Prothioconazole
in Benzyl Acetate/AMD810/Cyclohexanone Blends at 10° C.

| | Solvent Ratio (weight fraction) | | | | |
|---|---|---|---|---|---|
| Blend Number | Cyclohexanone[2] | Benzyl acetate | AMD810 | Compound A | Prothioconazole |
| | | | | Solubility (% w/w) @ 10° C. | |
| 1 | 0 | 0 | 1 | 3.3 | 34.3 |
| 2 | 0 | 0.2 | 0.8 | 4.3 | 32.3 |
| 3 | 0.2 | 0 | 0.8 | 4.5 | 33.9 |
| 4 | 0.2 | 0.2 | 0.6 | 6.2 | 32.9 |
| 5 | 0 | 0.4 | 0.6 | 6.5 | 33.1 |
| 6 | 0.2 | 0.4 | 0.4 | 10.5 | 32.1 |
| 7 | 0 | 0.6 | 0.4 | 11 | 32.1 |
| 8 | 0 | 0.8 | 0.2 | 12 | 26.6 |
| 9 | 0.13 | 0.62 | 0.25 | not tested | not tested |
| 10 | 0.2 | 0.6 | 0.2 | 13.6 | 29.9 |

TABLE 11-continued

Solubility of Compound A and Prothioconazole
in Benzyl Acetate/AMD810/Cyclohexanone Blends at 10° C.

| Blend Number | Solvent Ratio (weight fraction) | | | Compound A Solubility (% w/w) @ 10° C. | Prothioconazole |
|---|---|---|---|---|---|
| | Cyclohexanone[2] | Benzyl acetate | AMD810 | | |
| 11 | 0 | 1 | 0 | 14.3 | 16.2 |
| 12 | 0.2 | 0.8 | 0 | 15.2 | 18.4 |

Example 3

Storage Stability of Representative Samples of the Described Fungicidal Composition a) Accelerated Storage Stability Study of Compound A in Liquid Compositions Comprising Benzyl Acetate. AMD 810 and a Third Solvent.

The stability of Compound A in a variety of liquid compositions stored at 54° C. for 2 weeks is shown in Table 12. The test compositions were prepared in a manner similar to that described in Example 1 using one or more of Compound A, prothioconazole, pyraclostrobin, benzyl acetate, and AMD 810, and a third solvent chosen from cyclohexanone, acetophenone, 2-heptanone, 2-heptanol, oleyl alcohol or 2-ethylhexanol.

Sample 1 was stored at −10° C. for 1 week in a closed container following CIPAC Method 39.3. The sample remained as a clear homogeneous yellow liquid with no crystallization occurring.

Sample 1 was stored in a closed container at freeze-thaw conditions where the temperature was cycled between −10° C. and 40° C. every 24 hours for 4 weeks. The sample remained as a homogeneous liquid after storage.

b) Dilution of Sample 1 in Rt Water:

Following CIPAC Method 36.3, a 1 mL aliquot of Sample 1 was diluted in 100 mL of 342 ppm hardness water at room temperature to readily form a uniform, oil-in-water emulsion that maintained its stability at rt for at least 24 hours. No crystallization of Compound A was evident in the emulsion.

TABLE 12

Stability of Compound A in Liquid Compositions
Comprising Benzyl Acetate, AMD 810 and a Third Solvent
after Storage for 2 Weeks at 54° C.

| Composition (wt %) | | | | | | | Compound A after Storage (% retention)[1] |
|---|---|---|---|---|---|---|---|
| Compound A | Prothioconazole | Pyraclostrobin | Benzyl acetate | AMD 810 | Third Solvent | Third Solvent | |
| 4.9 | — | — | 94.1 | — | — | none | 85 |
| 3.4 | — | — | — | 96.0 | — | none | 49 |
| 12.0 | — | — | — | — | 85.7 | cyclohexanone | 96 |
| 4.9 | 7.4 | — | 46.8 | 25.2 | — | none | 91[2] |
| 4.9 | — | 5.0 | 48.4 | 26.0 | — | none | 92[2] |
| 4.1 | — | 5.2 | 37.0 | 20.0 | 8.2 | cyclohexanone | 93[2] |
| 4.9 | — | 6.3 | 44.4 | 23.9 | 4.9 | acetophenone | 94[2] |
| 4.9 | — | 6.3 | 44.4 | 23.9 | 4.9 | 2-heptanone | 93[2] |
| 4.9 | — | 6.3 | 44.4 | 23.9 | 4.9 | oleyl alcohol | 92[2] |
| 4.9 | — | 6.3 | 44.4 | 23.9 | 4.9 | 2-ethyl hexanol | 96[2] |
| 4.9 | — | 6.3 | 44.4 | 23.9 | 4.9 | 2-heptanol | 94[2] |
| 7.7 | — | 9.8 | 37.1 | 20.0 | 9.6 | cyclohexanone | 97 |
| 4.9 | — | 6.3 | 41.2 | 22.2 | 9.8 | cyclohexanone | 98 |
| 5.0 | — | 6.4 | 40.9 | 22.0 | 10.0 | 2-ethyl hexanol | 95 |
| 7.8 | — | 9.9 | 36.7 | 19.8 | 9.7 | 2-ethyl hexanol | 97 |

[1]Determined by HPLC analysis;
[2]Composition includes an emulsifier blend (14.7 wt %) comprising calcium dodecylbenzene sulfonate, butanol ethylene oxide/propylene oxide block polymer, and tridecyl alcohol ethoxylate.

Example 4

Storage Stability and Dilution of Sample 1 in Water a) Storage Stability of Sample 1:

Sample 1 was stored at 54° C. for 2 weeks in a closed container. The sample remained as a clear, homogeneous yellow liquid with no solids formation or phase separation during the storage period. HPLC analysis showed 97.6% retention of Compound A after the storage period.

c) Dilution of Sample 1 in 5° C. Water:

Following CIPAC Method 36.3, a 1 mL aliquot of Sample 1 was diluted in 100 mL of 342 ppm hardness water at 5° C. to readily form a uniform, oil-in-water emulsion that maintained its stability at rt for at least 24 hours. No crystallization of Compound A was evident in the emulsion.

d) Storage Stability of Sample 6:

Sample 6 was stored at 54° C. for 2 weeks in a closed container. The sample remained as a clear, homogeneous yellow liquid with no solids formation or phase separation during the storage period. HPLC analysis showed 91% retention of Compound A after the storage period.

e) Storage Stability of Sample 7:

Sample 7 was stored at 54° C. for 2 weeks in a closed container. The sample remained as a clear, homogeneous yellow liquid with no solids formation or phase separation during the storage period. HPLC analysis showed 91% retention of Compound A after the storage period.

Example 5

Evaluation of the Described Fungicidal Compositions for Disease Control a) Comparison of Disease Control Using 3 EC Formulations Comprising Active Ingredient Compound A that Differ in their Water Immiscible Organic Solvent Composition.

Methods: The fungicide formulations comprising Compound A were applied to wheat seedlings (2 leaf stage) with the use of a track sprayer (Devris) in a spray volume equal to 200 l/ha. Five concentrations of active ingredient were used. The concentrations used were 40.3, 13.4, 4.48 and 1.49 g ai/ha. Plants were inoculated in 3 day curative (3DC) and one day protectant (1DP) tests. Plants were challenged with both PUCCRT (*Puccinia triticina*; wheat brown rust) and SEPTTR (*Septoria tritici*; wheat leaf blotch) fungal pathogens. A total of 3 replications were used for each timing and pathogen combination. Disease caused by PUCCRT was evaluated 7 days after inoculation and disease caused by SEPTTR was evaluated 18-21 days after inoculation. The % tissue infected was determined and then the % disease control was calculated using the following equation: % disease control=(1-observed disease/disease from the untreated)*100.

Materials: The emulsifiable concentrate (EC) formulations shown in Table 13 were used in fungicide spray applications for the control of *Septoria tritici* (wheat leaf blotch) and *Puccinia triticina* (wheat brown rust) on wheat plants. The Sample A and Sample B comparative formulations comprised of cyclohexanone/Aromatic 100 and N-methylpyrrolidone/Aromatic 200ND, respectively, as the water immiscible organic solvents, whereas the Sample C formulation comprised of benzyl acetate:N,N-dimethyl fatty acid amide as the water immiscible organic solvent.

TABLE 13

Composition of EC Formulations Used in Fungicide Spray Applications

| Formulation | Type | Component | Role | Conc. g/L |
|---|---|---|---|---|
| Sample A | EC | Compound A | Active Ingredient | 70.0 |
| | | Tensiofix N9811HF | Emulsifier | 14 |
| | | Tensiofix N9839HF | Emulsifier | 98 |
| | | cyclohexanone | Solvent | 223.9 |
| | | Aromatic 100 | Solvent | 527.1 |
| Sample B | EC | Compound A | Active Ingredient | 100.0 |
| | | Sponto 300T | Emulsifier | 11 |
| | | Sponto 500T | Emulsifier | 43 |
| | | N-methyl pyrrolidone | Solvent | 423 |
| | | Aromatic 200ND | Solvent | 423 |
| Sample C | EC | Compound A | Active Ingredient | 50 |
| | | co/po block copolymer | Emulsifier | 30 |
| | | calcium dodecylbenzene sulfonate | Emulsifier | 75 |
| | | tridecyl alcohol, ethoxylated | Emulsifier | 45 |
| | | benzyl acetate | Solvent | 517.3 |
| | | N,N-dimethyl fatty acid amide | Solvent | 287.7 |

Disease Control Data: Table 14 shows the average disease control of fungicide spray applications for the control of *Septoria tritici* (SEPTTR; wheat leaf blotch) and *Puccinia triticina* (PUCCRT; wheat brown rust) on wheat plants.

TABLE 14

Disease Control on Wheat Plants with Various Spray Applied Formulations Comprising Compound A

| Formulation Applied | Pathogen and Application Timing | Compound A Application Rate (g ai/ha) | | | |
|---|---|---|---|---|---|
| | | 1.47 | 4.48 | 13.4 | 40.3 |
| | | Average % Disease Control | | | |
| none - inoculated | PUCCRT 1DP | 0 | 0 | 0 | 0 |
| none - clean | PUCCRT 1DP | 100 | 100 | 100 | 100 |
| Sample A - comparative | PUCCRT 1DP | 17 | 27 | 97 | 99 |
| Sample B - comparative | PUCCRT 1DP | 19 | 44 | 90 | 98 |
| Sample C | PUCCRT 1DP | 50 | 90 | 99 | 100 |
| Sample C + Trycol 5941 | PUCCRT 1DP | 80 | 99 | 100 | 100 |
| none - inoculated | PUCCRT 3DC | 0 | 0 | 0 | 0 |
| none - clean | PUCCRT 3DC | 100 | 100 | 100 | 100 |
| Sample A - comparative | PUCCRT 3DC | 0 | 0 | 0 | 22 |
| Sample B - comparative | PUCCRT 3DC | 0 | 0 | 0 | 18 |
| Sample C | PUCCRT 3DC | 0 | 0 | 16 | 73 |
| Sample C + Trycol 5941 | PUCCRT 3DC | 0 | 0 | 22 | 87 |
| none - inoculated | SEPTTR 1DP | 0 | 0 | 0 | 0 |
| none - clean | SEPTTR 1DP | 100 | 100 | 100 | 100 |
| Sample A - comparative | SEPTTR 1DP | 21 | 19 | 59 | 67 |
| Sample B - comparative | SEPTTR 1DP | 4 | 13 | 29 | 90 |
| Sample C | SEPTTR 1DP | 17 | 45 | 97 | 100 |
| Sample C + Trycol 5941 | SEPTTR 1DP | 47 | 83 | 91 | 96 |
| none - inoculated | SEPTTR 3DC | 0 | 0 | 0 | 0 |
| none - clean | SEPTTR 3DC | 100 | 100 | 100 | 100 |
| Sample A - comparative | SEPTTR 3DC | 86 | 93 | 95 | 97 |
| Sample B - comparative | SEPTTR 3DC | 75 | 87 | 88 | 97 |
| Sample C | SEPTTR 3DC | 71 | 93 | 100 | 100 |
| Sample C + Trycol 5941 | SEPTTR 3DC | 90 | 100 | 100 | 100 |

[1]Trycol 5941 (BASF; tridecyl alcohol-(EO)$_9$) is an adjuvant added to the respective spray solutions at a concentration of 0.05 wt % to boost fungicide efficacy.

b) Disease Control Using Described Compositions Comprising Compound A and, Optionally, Either Prothiconazole or Pyraclostrobin, Before and after a Simulated Rain Event to Evaluate Rainfastness of the Applied Compositions.

Methods: 'Yuma' wheat was used as the host plant in these fungicide efficacy trials. Seedlings were sprayed when the second leaf was fully expanded (8 days after seeding). The fungus *Puccinia triticina* (PUCCRT: wheat brown rust) was used as the test organism in the efficacy bioassay. The amount of rain applied after fungicide applications was 10 mm. Four separate rain treatments were used with each fungicide treatment. The rain treatments were no rain, and rain at 1, 30, or 60 minutes after fungicide application. There were three replicate for each combination of fungicide, rate, and rainfall interval. All fungicide formulations were diluted in water to achieve the desired spray concentrations. Fungicides were applied with a track sprayer set at 150 liters per hectare delivery volume at 2.1 atm and a speed of 1.9 km/h. A flat fan TeeJet 8003 nozzle tip was used. The nozzle tip was 50 cm above the top of the seedlings. All fungicide formulations were applied at ¼, ⅛ and 1/16 of the recommended field rate (1×). Table 15 shows the results from these trials.

TABLE 15

Disease Control on Wheat Plants with Various Spray Applied Formulations Comprising Compound A after Simulated Rain Events

| Active Ingredient (1X Rate) | Formulation | Weather event | % Disease Control of PUCCRT 1DP at Indicated Rate of Application[1] ¼X | ⅛X | 1/16X |
|---|---|---|---|---|---|
| Compound A (130 g ai/ha) | Sample 1 | no rain | 100 | 100 | 98 |
| | | rain at 1 minute | 100 | 99 | 95 |
| | | rain at 30 minutes | 100 | 98 | 92 |
| | | rain at 60 minutes | 100 | 98 | 92 |
| Compound A + prothioconazole (100 + 200 g ai/ha) | Sample 2 | no rain | 100 | 100 | 99 |
| | | rain at 1 minute | 100 | 99 | 91 |
| | | rain at 30 minutes | 100 | 96 | 81 |
| | | rain at 60 minutes | 100 | 97 | 91 |
| Compound A + prothioconazole (100 + 200 g ai/ha) | Sample 4 | no rain | 100 | 100 | 89 |
| | | rain at 1 minute | 100 | 99 | 61 |
| | | rain at 30 minutes | 100 | 98 | 56 |
| | | rain at 60 minutes | 100 | 99 | 50 |
| Compound A + pyraclostrobin (100 + 125 g ai/ha) | Sample 5 | no rain | 100 | 100 | 99 |
| | | rain at 1 minute | 100 | 100 | 83 |
| | | rain at 30 minutes | 100 | 100 | 90 |
| | | rain at 60 minutes | 100 | 99 | 89 |

[1]The application rate for each active ingredients are ¼, ⅛, and 1/16, respectively, of the 1X rate shown in column 1 for the respective active ingredient.

The entire disclosures of (1) PCT Patent Application No. PCT/US15/68011, filed Dec. 30, 2015, titled FUNGICIDAL COMPOSITIONS; (2) PCT Patent Application No. PCT/US15/68018, filed Dec. 30, 2015, titled FUNGICIDAL COMPOSITIONS; and (3) PCT Patent Application No. PCT/US15/68019, filed Dec. 30, 2015, titled FUNGICIDAL COMPOSITIONS are expressly incorporated herein by reference.

The present invention is not limited in scope by the embodiments disclosed herein which are intended as illustrations of a few aspects of the invention and any embodiments which are functionally equivalent are within the scope of this invention. Various modifications of the processes, methods, and compositions in addition to those shown and described herein will become apparent to those skilled in the art and are intended to fall within the scope of the appended claims. Further, while only certain representative combinations of the process and method steps and composition components disclosed herein are specifically discussed in the embodiments above, other combinations of the composition components and process and method steps will become apparent to those skilled in the art and also are intended to fall within the scope of the appended claims. Thus a combination of components or steps may be explicitly mentioned herein; however, other combinations of components and steps are included, even though not explicitly stated. The term comprising and variations thereof as used herein is used synonymously with the term including and variations thereof and are open, non-limiting terms.

What is claimed:

1. A fungicidal composition comprising:

a) a fungicidal compound of Formula

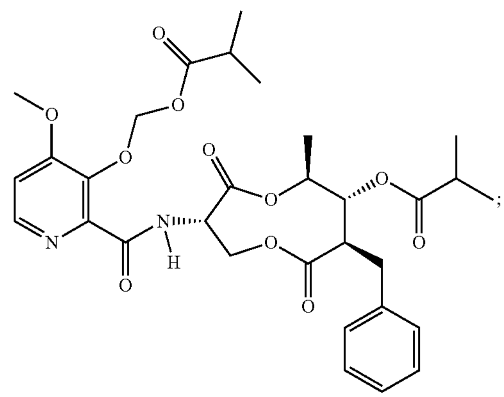 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

;

b) at least one ionic surfactant;

c) at least one nonionic surfactant;

d) from about 50 g/L to about 700 g/L of benzyl acetate; and e) at least one N,N-dialkylcarboxamide;

wherein the benzyl acetate and the at least one N,N-dialkylcarboxamide together form a water immiscible organic solvent.

2. The fungicidal composition of claim 1, wherein the composition includes:

a) from about 1 gram per liter (g/L) to about 200 g/L of the fungicidal compound of the Formula

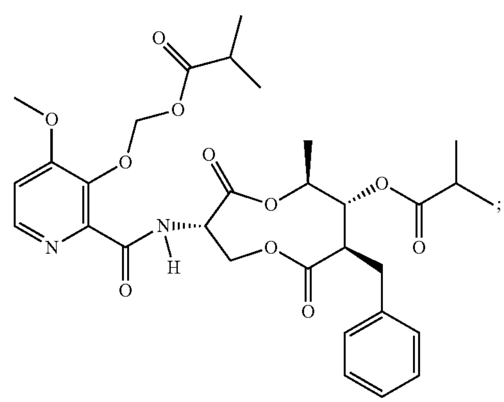 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

;

b) from about 1 g/L to about 100 g/L of the at least one ionic surfactant, wherein the at least one ionic surfactant includes at least one anionic surfactant;

c) from about 1 g/L to about 200 g/L of the at least one nonionic surfactant;

d) from about 50 g/L to about 700 g/L of benzyl acetate; and e) from about 25 g/L to about 300 g/L of the at least one N,N-dialkylcarboxamide, wherein the at least one N,N-dialkylcarboxamide includes an N,N-dimethyl fatty acid amide.

3. The fungicidal composition of claim 1, wherein the composition includes from about 1 gram per liter (g/L) to about 200 g/L of the fungicidal compound of the Formula

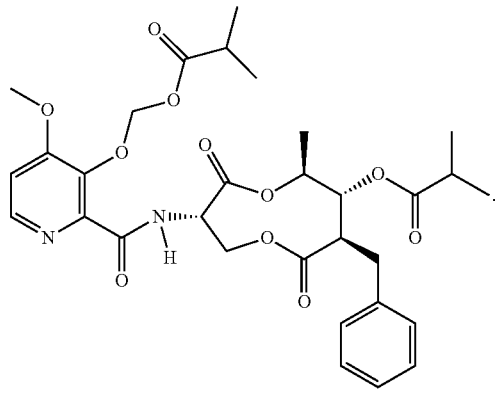 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

4. The fungicidal composition of claim 1, wherein the composition includes from about 1 g/L to about 100 g/L of the at least one ionic surfactant, wherein the at least one ionic surfactant includes at least one anionic surfactant.

5. The fungicidal composition of claim 1, wherein the composition includes from about 1 g/L to about 200 g/L of the at least one nonionic surfactant.

6. The fungicidal composition of claim 1, wherein the composition includes from about 25 g/L to about 300 g/L of the at least one N,N-dialkylcarboxamide, wherein the at least one N,N-dialkylcarboxamide includes at least one of an N,N-dimethyl fatty acid amide.

7. The fungicidal composition of claim 1, wherein the weight ratio of the at least one acetate ester:the at least one N,N-dialkylcarboxamide ranges from about 1-10:1-10.

8. The fungicidal composition of claim 1, wherein the weight ratio of the at least one acetate ester : the at least one N,N-dialkylcarboxamide ranges from about 1-5:1-2.

9. The fungicidal composition of claim 1, wherein the at least one N,N-dialkylcarboxamide is selected from a group consisting of N,N-dimethylhexanamide, N,N-dimethyloctanamide, N,N-dimethyldecanamide and N,N-dimethyldodecanamide.

10. The fungicidal composition of claim 1, further including at least one additional fungicidal compound.

11. The fungicidal composition of claim 10, wherein the at least one additional fungicidal compound is selected from a group consisting of azoxystrobin, bifujunzhi, coumethoxystrobin, coumoxystrobin, dimoxystrobin, enestroburin, enoxastrobin, fenaminstrobin, fenoxystrobin, flufenoxystrobin, fluoxastrobin, jiaxiangjunzhi, kresoxim-methyl, mandestrobin, metominostrobin, orysastrobin, picoxystrobin, pyraclostrobin, pyrametostrobin, pyraoxystrobin, triclopyricarb, trifloxystrobin, methyl 2-[2-(2,5-dimethylphenyloxymethyl)phenyl]-3-methoxyacrylate, azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, imazalil, pefurazoate, prochloraz, triflumizole, pyrimidines, fenarimol, nuarimol, pyrifenox, and triforine.

12. The fungicidal composition of claim 1, further including an adjuvant that improves the fungicidal performance of the composition selected from a group consisting of a non-ionic surfactant, a polyether modified organopolysiloxane and an alkyl phosphonate.

13. A method of controlling fungal plant pathogens or diseases comprising the steps of contacting the vegetation or an area adjacent thereto to prevent the growth of the fungal pathogens or diseases with a fungicidally effective amount of a fungicidal composition comprising:

a) a fungicidal compound of Formula

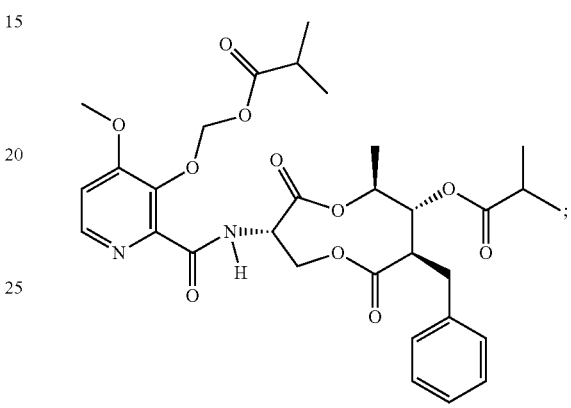

b) at least one ionic surfactant;

c) at least one nonionic surfactant;

d) from about 50 g/L to about 700 g/L of benzyl acetate; and e) at least one N,N-dialkylcarboxamide;

wherein the benzyl acetate and the at least one N,N-dialkylcarboxamide together form a water immiscible organic solvent.

14. The method of claim 13, wherein the at least one additional fungicidal compound is selected from a group consisting of azoxystrobin, bifujunzhi, coumethoxystrobin, coumoxystrobin, dimoxystrobin, enestroburin, enoxastrobin, fenaminstrobin, fenoxystrobin, flufenoxystrobin, fluoxastrobin, jiaxiangjunzhi, kresoxim-methyl, mandestrobin, metominostrobin, orysastrobin, picoxystrobin, pyraclostrobin, pyrametostrobin, pyraoxystrobin, triclopyricarb, trifloxystrobin, methyl 2-[2-(2,5-dimethylphenyloxymethyl)phenyl]-3-methoxyacrylate, azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, imazalil, pefurazoate, prochloraz, triflumizole, pyrimidines, fenarimol, nuarimol, pyrifenox, and triforine.

15. A fungicidal composition, comprising at least one fungicidal composition selected from the group of compositions consisting of:

a first fungicidal composition of Formula comprising
  a) a fungicidal composition of Formula

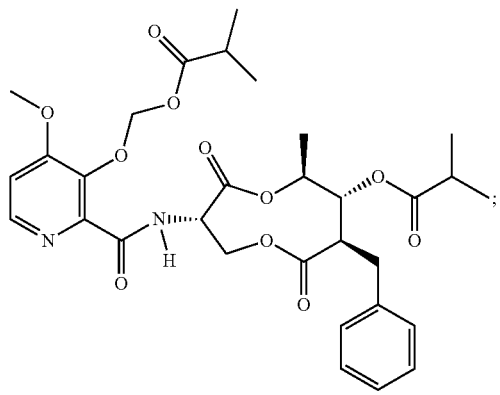 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

b) a calcium salt of an alkylaryl sulfonate;
  c) an alcohol initiated EO/PO block copolymer;
  d) a tridecyl alcohol ethoxylate;
  e) a polyether modified organopolysiloxane;
  f) from about 50 g/L to about 700 g/L of benzyl acetate; and
  g) an N,N-dimethyl fatty acid amide;
a second fungicidal composition comprising:
  a) a fungicidal compound of Formula

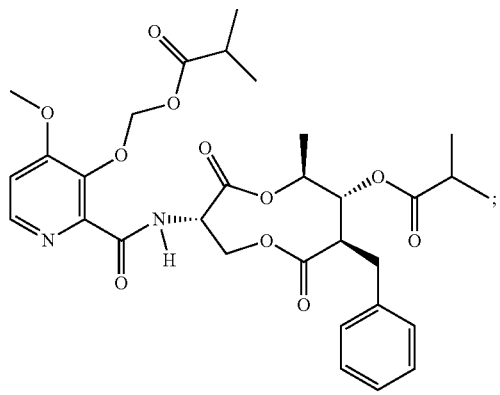 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

b) prothioconazole;
  c) a calcium salt of an alkylaryl sulfonate;
  d) an alcohol initiated EO/PO block copolymer;
  e) a tridecyl alcohol ethoxylate;
  f) a polyether modified organopolysiloxane;
  g) from about 50 g/L to about 700 g/L of benzyl acetate; and
  h) an N,N-dimethyl fatty acid amide;

a third fungicidal composition comprising:
  a) a fungicidal compound of Formula

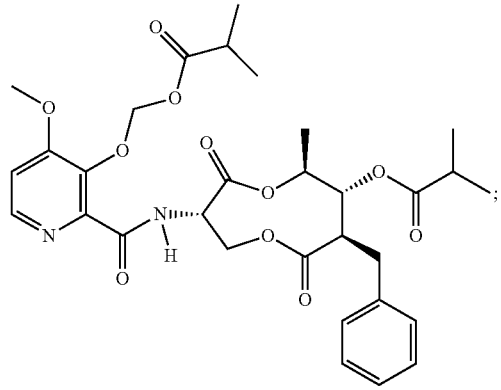 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

b) pyraclostrobin;
  c) an calcium salt of an alkylaryl sulfonate;
  d) an alcohol initiated EO/PO block copolymer;
  e) a tridecyl alcohol ethoxylate;
  f) a polyether modified organopolysiloxane;
  g) from about 50 g/L to about 700 g/L of benzyl acetate; and
  h) an N,N-dimethyl fatty acid amide;
  wherein the benzyl acetate and the N,N-dimethyl fatty acid amide together form a water immiscible organic solvent.

16. The fungicidal composition of claim 1, wherein the concentration of benzyl acetate is from about 300 g/L to about 500 g/L.

17. The fungicidal composition of claim 15, wherein the at least one fungicidal composition comprises:
  a) from about 20 g ai/L to about 100 g ai/L of the fungicidal composition of Formula

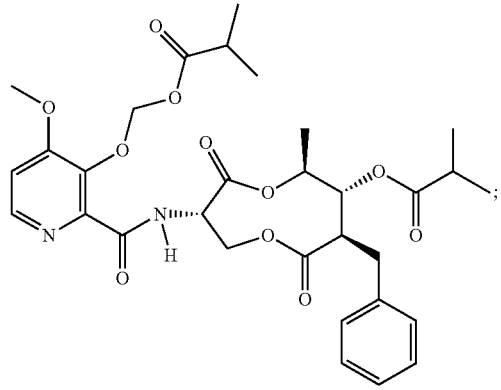 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

b) from about 20 g/L to about 100 g/L of calcium salt of an alkylaryl sulfonate;
  c) from about 20 g/L to about 160 g/L of alcohol initiated EO/PO block copolymer;
  d) from about 20 g/L to about 160 g/L of tridecyl alcohol ethoxylate;
  e) from about 20 g/L to about 150 g/L of polyether modified organopolysiloxane;

f) from about 100 g/L to about 700 g/L of benzyl acetate; and g) from about 100 g/L to about 300 g/L of N,N-dimethyl fatty acid amide.

18. The fungicidal composition of claim 15, wherein the at least one fungicidal composition comprises:

a) from about 20 g ai/L to about 100 g ai/L of the fungicidal compound of Formula

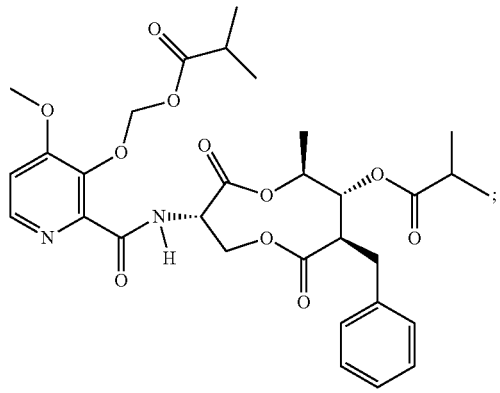 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

b) from about 50 g ai/L to about 150 g ai/L of prothioconazole;

c) from about 20 g/L to about 100 g/L of calcium salt of an alkylaryl sulfonate;

d) from about 20 g/L to about 160 g/L of alcohol initiated EO/PO block copolymer;

e) from about 20 g/L to about 160 g/L of tridecyl alcohol ethoxylate;

f) from about 20 g/L to about 150 g/L of polyether modified organopolysiloxane;

g) from about 100 g/L to about 700 g/L of benzyl acetate; and h) from about 100 g/L to about 300 g/L of N,N-dimethyl fatty acid amide.

19. The fungicidal composition of claim 15, wherein the at least one fungicidal composition comprises:

a) from about 20 g ai/L to about 100 g ai/L the fungicidal compound of Formula

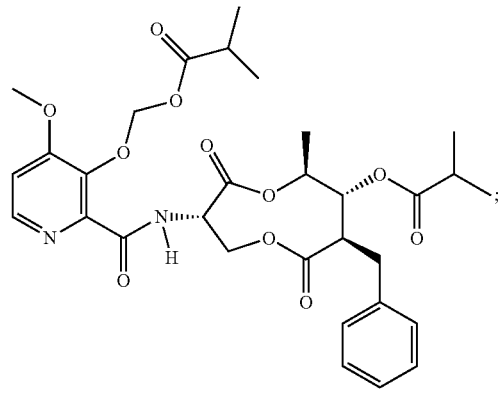 [SMILES: COc1ccnc(C(=O)N[C@H]2COC(=O)[C@H](Cc3ccccc3)[C@@H](OC(=O)C(C)C)[C@H](C)OC2=O)c1OCOC(=O)C(C)C]

b) from about 50 g ai/L to about 150 g ai/L pyraclostrobin;

c) from about 20 g/L to about 100 g/L of calcium salt of an alkylaryl sulfonate;

d) from about 20 g/L to about 160 g/L of alcohol initiated EO/PO block copolymer;

e) from about 20 g/L to about 160 g/L of tridecyl alcohol ethoxylate;

f) from about 20 g/L to about 150 g/L of polyether modified organopolysiloxane;

g) from about 100 g/L to about 700 g/L of benzyl acetate; and h) from about 100 g/L to about 300 g/L of N,N-dimethyl fatty acid amide.

20. The fungicidal composition of claim 11, wherein the at least one additional fungicidal compound comprises propiconazole.

21. The fungicidal composition of claim 14, wherein the at least one additional fungicidal compound comprises propiconazole.

* * * * *